United States Patent
Keller et al.

(10) Patent No.: US 11,745,537 B1
(45) Date of Patent: *Sep. 5, 2023

(54) REUSABLE BODY ART STENCIL

(71) Applicant: John Brent Mötteli, Arbon (CH)

(72) Inventors: Michelle Alexandra Keller, Sun City Center, FL (US); John Brent Moetteli, Arbon (CH)

(*) Notice: Subject to any disclaimer, the term of this patent is extended or adjusted under 35 U.S.C. 154(b) by 1,387 days.

This patent is subject to a terminal disclaimer.

(21) Appl. No.: 16/134,995

(22) Filed: Sep. 19, 2018

Related U.S. Application Data

(63) Continuation-in-part of application No. 14/797,256, filed on Jul. 13, 2015, now Pat. No. 10,279,620.
(Continued)

(51) Int. Cl.
| | |
|---|---|
| A45D 40/30 | (2006.01) |
| B44D 2/00 | (2006.01) |
| A45D 34/04 | (2006.01) |

(Continued)

(52) U.S. Cl.
CPC ............. *B44D 2/007* (2013.01); *A45D 34/04* (2013.01); *A45D 40/262* (2013.01); *B44D 2/002* (2013.01); *A45D 2200/25* (2013.01); *A61K 8/00* (2013.01); *A61M 35/003* (2013.01)

(58) Field of Classification Search
CPC ... A45D 40/30; A45D 2200/1081; D44D 2/007
See application file for complete search history.

(56) References Cited

U.S. PATENT DOCUMENTS

| | | | |
|---|---|---|---|
| 1,854,821 | A | 4/1932 | Barker |
| 2,695,622 | A | 11/1954 | Herod et al. |
| 2,917,058 | A | 12/1959 | Ferrar |
| 3,633,286 | A | 1/1972 | Maurer |
| 5,052,418 | A | 10/1991 | Miller |
| 5,186,190 | A | 2/1993 | Hirzel |

(Continued)

FOREIGN PATENT DOCUMENTS

| | | | |
|---|---|---|---|
| CA | 2 727 849 | A1 | 7/2012 |
| DE | 34 20 867 | A1 | 12/1985 |

(Continued)

OTHER PUBLICATIONS

European Search Report, European patent application No. 17178208.9, Mar. 1, 2018.

*Primary Examiner* — Kurt Fernstrom
(74) *Attorney, Agent, or Firm* — Da Vinci Partners LLC; John Moetteli

(57) ABSTRACT

A system is provided enabling do it yourself body stencilling and/or body art. In particular, the system of the invention provides a body tight removable mask that masks an area of the body for body painting. The mask is sized to fit a particular portion of the torso or an appendage of a subject individual, and masks a standard area to enable an unskilled artist to paint a portion of the subject individual. The stencil can mask a logo of a sports team or other form such as a swimsuit form on a wrist or ankle or upper torso, forehead, or a bathing suit area of the subject individual. The system optionally includes adhesive, Velcro, or other interlocking overlapping portions enabling easy removal of the stencil without disturbing the freshly painted area. In its simplest form, the stencil is a mask of the thighs, and the waste, the lower chest area and upper chest area, for example, with a preferably elastic mask panel that can be easily removed once the basic painting is complete. Advantageously, the invention enables websites that feature body painting, such as Sports teams, Universities, Sports Illustrated or Fashion TV, to sell stencil product in association with displays of body painted models.

25 Claims, 25 Drawing Sheets

Related U.S. Application Data

(60) Provisional application No. 62/031,192, filed on Jul. 31, 2014, provisional application No. 62/025,020, filed on Jul. 16, 2014.

(51) Int. Cl.
*A45D 40/26* (2006.01)
*A61M 35/00* (2006.01)
*A61K 8/00* (2006.01)

(56) References Cited

U.S. PATENT DOCUMENTS

| | | | |
|---|---|---|---|
| 5,470,351 | A | 11/1995 | Ross et al. |
| 5,479,351 | A | 12/1995 | Woo et al. |
| 5,662,129 | A | 9/1997 | Grenevitch et al. |
| 5,816,269 | A | 10/1998 | Mohammed |
| 5,836,998 | A | 11/1998 | Mueller et al. |
| 6,096,154 | A | 8/2000 | Comiskey et al. |
| 6,106,852 | A | 8/2000 | Vineberg |
| 6,289,801 | B1 | 9/2001 | Raymond |
| 6,606,943 | B2* | 8/2003 | De Laforcade .. B29C 45/14336 101/127.1 |
| 6,881,253 | B2* | 4/2005 | Dhuey ................. A61K 8/046 8/404 |
| 8,118,851 | B1* | 2/2012 | Kurzmiller .......... A61N 5/0614 428/137 |
| 9,193,144 | B2* | 11/2015 | Heijningen ............. B32B 7/06 |
| 10,820,680 | B1* | 11/2020 | Macri .................... A45D 40/30 |
| 11,338,308 | B2* | 5/2022 | Asami et al. ......... B05B 5/1675 |
| 2001/0047951 | A1 | 12/2001 | O'Connor |
| 2005/0205105 | A1* | 9/2005 | Demko .............. A45D 19/012 132/214 |
| 2006/0121097 | A1 | 6/2006 | Lodge et al. |
| 2006/0249173 | A1 | 11/2006 | Lawson |
| 2007/0006748 | A1* | 1/2007 | Liu ....................... A45D 40/30 101/127 |
| 2009/0120565 | A1 | 5/2009 | Marshall |
| 2009/0266377 | A1* | 10/2009 | Matsumoto et al. ... A61Q 1/025 132/202 |
| 2009/0317774 | A1 | 12/2009 | Sharp |
| 2013/0319443 | A1* | 12/2013 | See .................... A61K 8/0241 132/200 |
| 2015/0296960 | A1 | 10/2015 | Samaco, III |
| 2015/0359318 | A1 | 12/2015 | Martin et al. |
| 2018/0272797 | A1* | 9/2018 | Allenspach et al. ...... B05B 12/24 |
| 2018/0360739 | A1* | 12/2018 | Lorenz et al. ......... A61K 47/22 |

FOREIGN PATENT DOCUMENTS

| | | |
|---|---|---|
| DE | 202 15 489 U1 | 1/2003 |
| EP | 0 962 155 A1 | 12/1999 |
| EP | 1 611 815 A1 | 1/2006 |
| FR | 2 705 615 A1 | 12/1994 |
| NL | 1024119 C1 | 10/2003 |
| WO | 2005/070386 A1 | 8/2005 |

\* cited by examiner

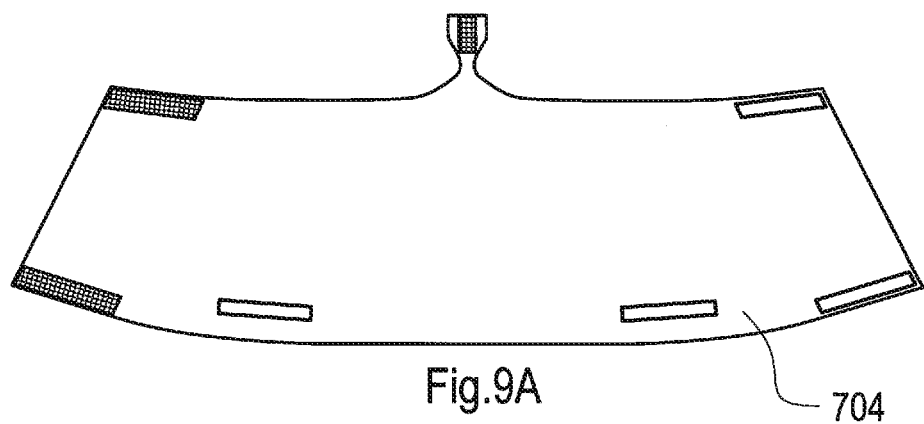
Fig.9A — 704
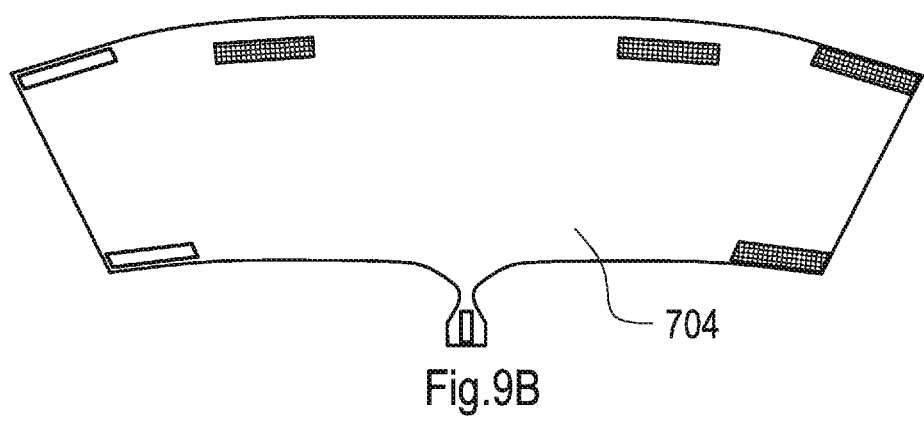
Fig.9B — 704

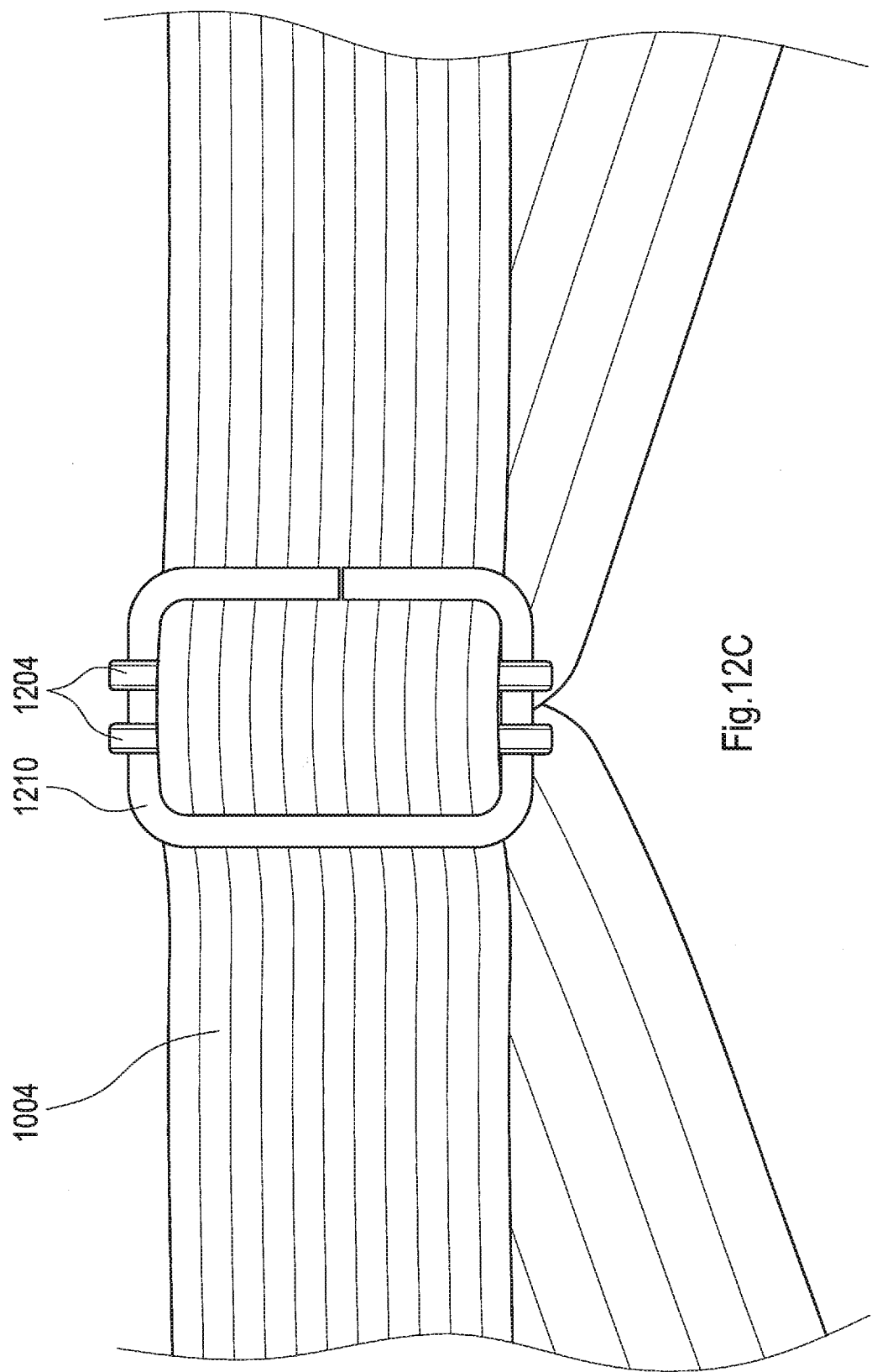

REUSABLE BODY ART STENCIL

CROSS REFERENCE TO RELATED APPLICATIONS

This application is a continuation in part application of application serial no. 14/797,256, of the same title, filed Jul. 13, 2015 which claims priority to U.S. Provisional applications 62/025,020 filed Jul. 16, 2014 and U.S. Provisional Application no. 62/031,192 filed Jul. 31, 2014, the contents of which are incorporated by reference and relied upon.

COPYRIGHT & LEGAL NOTICE

A portion of the disclosure of this patent document contains material which is subject to copyright protection. The Applicant has no objection to the facsimile reproduction by anyone of the patent document or the patent disclosure as it appears in the Patent and Trademark Office patent file or records, but otherwise reserves all copyright rights whatsoever. Further, no references to third party patents or articles made herein is to be construed as an admission that the present invention is not entitled to antedate such material by virtue of prior invention.

BACKGROUND OF THE INVENTION

This invention relates to stencils for body painting on individuals, and in particular, stencils that can be reused on humans.

Body painting, or sometimes bodypainting, is a form of body art. Unlike tattoo and other forms of body art, body painting is temporary, painted onto the human skin, and lasts for only several hours, or at most (in the case of Mehndi or "henna tattoo") several weeks. Body painting that is limited to the face is known as face painting. Body painting is also referred to as (a form of) "temporary tattoo"; large scale or full-body painting is more commonly referred to as body painting, while smaller or more detailed work is generally referred to as temporary tattoos.

Body stencils exist and are made up of simple patterns formed in a typically flexible but flat substrate. Such are effective for applying a simple, detail form such as a flower or heart, but are not effective for applying a form that follows the contours of a torso or appendage of a subject individual. These forms are typically much more elaborate and tend to flow from the front of the human torso around the side of the torso and onto the back of the torso.

It is also known to place netting or some other repeating pattern against the body, and paint using the netting as a stencil. Sometimes body netting is donned, then local painting is performed, the netting removed to leave only the repeated patterns. Sports Illustrated's body painting of model Hanna Ferguson was performed in this way. Inspection of the video of the body painting session makes clear that simple towels or other improvised masks were used to control overspray. The netting patterns itself does not provide any overspray protection to the overall pattern to be painted.

Consequently, body painting has generally been limited to the realm of the experienced artist. This is in part because professional air brushes must be used to obtain clearly defined lines, instead of typical cans of body spray paint. Body paint spray exists but because of the significant overspray, does not provide defined delineations between painted and unpainted or other painted (painted with another color) areas. Because precise demarcation between painted and unpainted or other color painted areas is necessary to create readable designs on an epidermal area, spray cans are typically only used as a background color over which hand painted paints are applied.

Henna based dyes or paintings are utilized to apply various designs to temporarily decorate the epidermis in various cultures, e.g. the Middle Eastern, Indian and North Carican cultures. This is done by applying the paste directly to the epidermis, either free hand or through the use of a stencil. These methods can be difficult to use for the novice. The free hand method takes experience, control, is time consuming and expensive. Stencils can leak and are hard to keep in place.

Mehndi is an art form in which henna based epidermal dye is applied to painting the skin in decorative patterns and has been known for many centuries. This art form is still used primarily in Middle Eastern and Asian cultures before a celebration such as a wedding or a festival. For example, Hindu women have intricate designs applied to their palms and soles of their feet prior to their wedding because, for example, it is believed that the designs enhance fertility and the chance that the young couple will have children. To others, the decorative patterns are aesthetically pleasing and enhances the beauty of the bride. After the henna paste is applied to the skin and allowed to dry, it will painted on the epidermal layer of the skin in direct contrast to a tattoos in which the entire dermis is painted. The epidermis, or outer layer of the skin, naturally sloughs off and takes the Mehndi design with it over time. In effect, the individual has a tattoo that will naturally disappear in one to four weeks depending on a variety of factors. The duration depends on the location of the body to which the painting is applied, the uptake of the paint pigment, and the exposure of the epidermal area to which the paint is applied. For example, the epidermis is thicker on the sole of the foot than on the face, so a Mehndi design that is applied to the sole of the foot will last longer than one that is applied to the face. Further, the Mehndi designs will not last as long when the person having the design constantly washes their hands or other body part, or is exposed to chemicals that remove or dry the epidermis increases sloughing of the skin and correspondingly decreases the duration of the decorative Mehndi painting.

There are a number of undesirable features associated with the application of decorative Mehndi paintings also, as with Western body art. First, having Mehndi and body art applied by a trained artist is costly. Second, the majority of the public does not have the artistic training needed to produce a design and have a satisfying result. Third, if the henna paste comes in contact with any exposed skin, then it will leave a mark, even if left on for a brief period of time. Fourth, if the henna past is not of the correct consistency, it will bleed beyond the line drawn and causing widening or blurring of the line that was intended to be drawn by the person applying the painting. Outside of Mehndi paintings, body art painting has grown in popurality with various marketers of goods and promoters of services, such as grande openings of establishments including bars, casinos, hotels and the like in Eastern Europe, as well as for entertainers and dancers where there are theme parties at various night clubs and other venues. Full body art by a professional is both time consuming and entails expense, and requires expertise.

Exemplary art in the area of body/face painting include: U.S. Pat. Nos. 5,836,998, 5,052,418, 5,816269, and 5,479,351; and U.S. Pat. Publication Nos. 2009/317774, 2006/1211097, 20001/047951, CA2727849, NL1024119, EP1611815. Similar art that is not for parts of the body below the neck art includes: U.S. Pat. Publication No. 2006/121097, 2009/120565, and U.S. Pat. No. 6,289,801. Non-analagous art related to suntaning methods and "paint coated body parts" that are used to producing art on surfaces other than the human body, e.g. a human paint brush, includes: DE20215489, DE3420867, WO2005070386, FR2705616, FR2705615, and U.S. Pat. Publication No. 2009/317774.

What is needed therefore is a system and method enabling inexperienced artists to apply a standard base color coat to a subject individual on which other patterns and details may optionally be applied so that a very aesthetically pleasing result is obtained.

SUMMARY OF THE INVENTION

The system of the invention provides a body tight removable mask that masks an area of the body of a mammal (a human person or animal, herein subsequently referred to as an individual) for body painting. The mask is sized to fit a particular portion of the torso or an appendage of a subject individual, and masks a standard area to enable an unskilled artist to paint a portion of the subject individual. The stencil can mask a logo of a sports team or other form such as a swimsuit form on a wrist or ankle or upper torso, forehead, or a bathing suit area of the subject individual. The system optionally includes adhesive, Velcro, or other interlocking overlapping portions enabling easy removal of the stencil without disturbing the freshly painted area.

In its simplest form, the stencil is a mask of the thighs, and the waste, the lower chest area and upper chest area, for example, with a preferably elastic mask panel that can be easily removed once the basic painting is complete. Advantageously, the invention enables websites that feature body painting, such as Sports teams, Universities, Sports Illustrated or Fashion TV, to sell stencil product in association with displays of body paintings.

In another feature, the mask can be turned inside out and so, if the pattern is asymmetrical, it will mask another area and so allow for painting multiple colors in a checker like manner.

In yet another aspect, the stencil is a mask of the thighs, and the waste, the lower chest area and upper chest area, for example, with a preferably elastic mask panel that can be easily removed once the basic painting is complete.

In yet a further variant, the invention provides a body stencil kit comprising the body stencil of any one or more of the elements and features described herein.

In yet a further aspect, the body stencil kit includes the body stencil system, further including at least one body paint and instructions for use.

In a variant, the kit further includes detail stencils for applying further detailing such as flowers or logos over the basic painting or over otherwise unpainted areas.

In yet another aspect, the invention provides a method for applying a decorative paint to the epidermis of a human. The method includes the steps of: applying a stencil having a decorative pattern formed therein around an appendage of a subject individual, masking thereby a predetermined area of the epidermis, the stencil comprising an removable interlocking overlapping panel for enabling easy removal of the stencil, the stencil itself providing an opaque essentially non-absorbent layer which protects the underlying epidermal area from an applied body paint, defining further an epidermal painting area; covering the epidermal painting area and a portion of the non-absorbant layer of the stencil with a predetermined amount of an epidermal painting material to cause the epidermal painting material to contact the epidermis only via the decorative pattern masked by the stencil; allowing the epidermal painting material to dry, a portion of the epidermal painting material covering the portion of the epidermis that is coextensive with the decorative pattern masked by the stencil to form a decorative painting in the epidermis in the form of the decorative pattern; and removing the stencil from the subject individual, thereby leaving the painted decorative pattern.

In a further variant, the epidermal painting material comprises a henna-based die.

In yet a further variant, the invention provides a system for creating body art on a mammal, the system that includes a three dimensionally conformable, skin tight mask. The mask includes one or more stencils, each of the stencils comprising a matrix of positioned bridging elements that permit aersol particulates to deposit below the bridging element onto the skin of the mammal.

In one aspect, the bridging elements are selected from the group consisting of bridging elements raised from one or more skin surfaces, and each respective bridging element is connected to at least a first mask and a second mask, and raised from a surface of the skin.

In another aspect, at least of portion of each of the stencils is made from a material that is less flexible than a material from which the remainder of the mask is constructed.

In another variant, the invention provides a kit for creating body art. The kit includes one or more body art spray cans, and one or more skin tight, elastic body art masks. Optionally, each of the respective masks have a first region and a second region, the first region being more elastic than the second region.

In one aspect, the body art masks are constructed to be conformable on the human body in three dimensions, and the kit further comprises body painting colour material, and brushes; make up, and supporting application brushes; costume apparel; hair styling elements, in which the hair styling elements are selected from the group consisting of hair spray, hair colour spray, and a head dress; and/or footwear.

In another variant, the invention provides a mask system for applying body art to an individual. The mask system includes a first removeable, substantially skin tight mask and a second removeable substantially skin tight mask. Each of the masks have corresponding stencils constructed thereon such that use of the combination of the first mask and the second mask, one after the other, permits the creation of a layered artwork region on the region of the individual's skin. Each of the layered artwork regions includes a substantially finished artwork region after the application of a second layer.

In one aspect, the first mask and the second mask are constructed to be re-useable.

These and other objects of the invention are readily apparent in the remainder of the specification including the detailed destription, drawings and claims.

BRIEF DESCRIPTION OF THE DRAWINGS

FIG. 9A is a top view of a waist component of the mask, laid flat.

FIG. 9B is a bottom view of the waist component of the mask, laid flat.

FIG. 10D is a fron view of the embodiment of FIG. 10A with snaps closed.

FIG. 12C is a close up view of the side view of FIG. 12B.

Those skilled in the art will appreciate that elements in the Figures are illustrated for simplicity and clarity and have not necessarily been drawn to scale. For example, dimensions may be exaggerated relative to other elements to help improve understanding of the invention and its embodiments. Furthermore, when the terms 'first', 'second', and the like are used herein, their use is intended for distinguishing between similar elements and not necessarily for describing a sequential or chronological order. Moreover, relative terms like 'front', 'back', 'top' and 'bottom', and the like in the Description and/or in the claims are not necessarily used for describing exclusive relative position. Those skilled in the art will therefore understand that such terms may be interchangeable with other terms, and that the embodiments described herein are capable of operating in other orientations than those explicitly illustrated or otherwise described.

DETAILED DESCRIPTION OF THE PREFERRED EMBODIMENT

The following description is not intended to limit the scope of the invention in any way as they are exemplary in nature, serving to describe the best mode of the invention known the inventors as of the filing date hereof. Consequently, changes may be made in the arrangement and/or function of any of the elements described in the exemplary embodiments disclosed herein without departing from the spirit and scope of the invention.

Figure 1A:
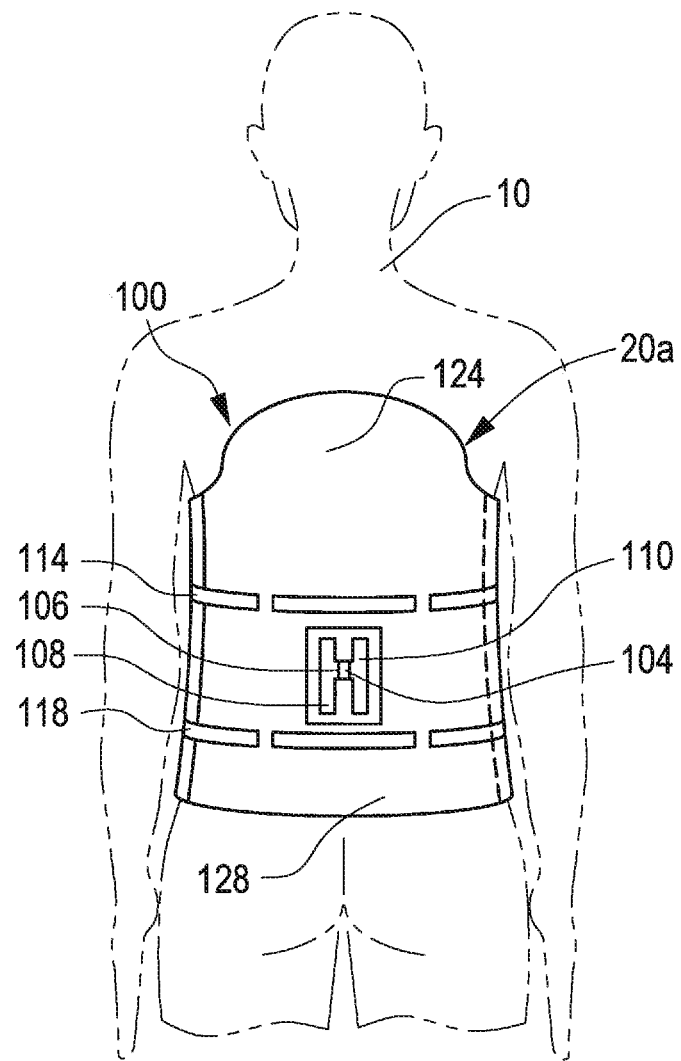
FIG. 1A is a front view of the system of the invention applied to a subject individual, around the chest.

Referring now to FIG. 1A, a front view of the system 100 of the invention applied to a subject individual, around the chest is shown. System 102 includes substantially rigid, less flexible backing material to maintain pattern form on application of colour or pigment onto the mammalian body using system 100. As referred to herein, the systems 100, et al., are used on the human body, however, the system(s) 100, et al., are also used on other animals, e.g. fish, insects, reptilians, birds and individuals, etc. System 100 further includes upper overspray panel 124 and lower overspray panel 128, with one or more intermediate overspray panels disposed/inserted therebetween. On system 100, 104 thin nylon fish line links (of course other polymeric material is also used in the invention as well as natural, bio-compatible materials) are provided to prevent deformation of pattern elements on application, the links are under tension or pressure in a native state. One or more patterns are provided across the front and back panels of system 100, as indicated by ornamental patterns 114, 118 on FIG. 1A. It is appreciated that the masks are single use disposable in one variant of the invention, and in another variant of the invention the masks are re-useable. In the context of the masks being re-useable, they are easily cleaned with solvents that are also biocompatible since the sprays used on the human body must be biocompatible so as not to irritate the skin.

Figure 1B:
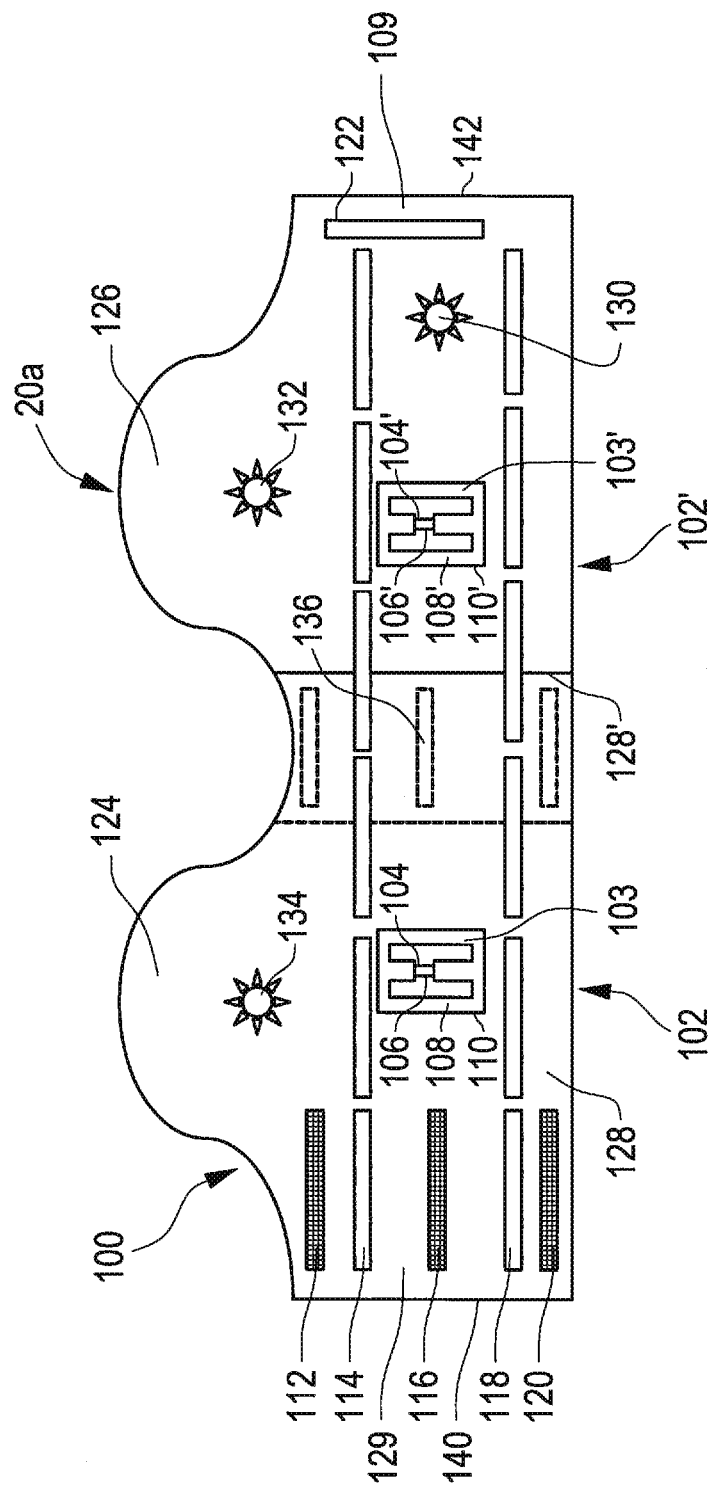
FIG. 1B is a top view of the mask of the system of FIG. 1A, laid flat.

Referring now to FIG. 1B, a top view of the mask of the system 100 of FIG. 1A, laid flat, is shown. Again, a plurality of aperature laden patterns 114, 116 are distributed in series across the length of system 100. Similarly, aperature laden patterns 130, 132, 134, 136 have the same or different aperature designs thereon, and are symmetrically or asymestrically distributed across the front, side and back panel portions of the system 100. It is appreciated that for larger designs the overspray panels 128, 124, and intervening panels, e.g. masks, are made of latex, neoprene, spandex, rubber or rubberized material, or other suitable flexible body conforming material. In other embodiments, the mask is made of spandex or other stretchable, elastic material. In another embodiment, the mask is made of nylon stocking material. Within the system 100 are subsystems 110, 110' of various stencils designs. These subsystems 110, 110' differ in elascticity from the other portions of the masks of the system 100, generally being more rigid, or less flexible while being able to at least partially conform to a portion of the human anatomy while not distorting the artistic design of the stencil and aperatures thereof.

To achieve this form of construction, the subsystems include fishnet material 102, through which spray colouring can pass, fish line or thin thread material 104, 106 through which colour, e.g. spray can pass, as well as other substantially rigid material 108 (a backing for example, which can be flat but is preferably formed so as to conform to the morphology of the body in that area so as to press against the skin at the painting edge) forming the stencil design 102 and are used to keep various elements of the stencil/mask in orientation to one another permiting the formation of the appropriate design on the skin. The elasticity of the combination of fishnet 102, or thread 104, 106, and/or rigid material 108 is optimally selected to match that of the material of the mask. In the variant of subsystem 110′, fishnet material 102′ has large aperatures therebetween so that there is no or very limited interference with the application of body spray paint to the skin is achieved, similarly a network of very thin threads 104′, 106′ are used to hold in various stencil element design elements. On or near the proximal end 140 of system 100 is located one or more re-openable interlocking fasteners which can be Velcro(tm) brand elements 112, 116, 120 which are spaced horizontally along the panel of system 100 to provide for adjustability of the system to fit more than size of human body portion. It is appreciated that the stencil is therefor infinitely adjustable around the torso of a human. Where centering of stencil forms on the check and on the back of the individual should be centered, then it is best that the stencil be comprised of two elements which interlock around the individual, so that the pattern can be centered front and back essentially regardless of the girth of the individual. This assumes tha the overlapping interlocks provide for interlocking over a significant circumferential range. This also help ensure that the stencil will not be significantly circumferentially stretched/deformed, so that the stencil pattern is not significantly deformed. At the distal end 142 of the system is a mating Velcro fastener 142 to that of fastener 140. The interlocking is preferably made through a Velcro interlock, but other mechanical interlocking means, such as buttons, clasps, clips etc. may be used. Further, adhesive and even magnetic interlocking means may be used to hold the mask in place against the skin. So a variety of fastener means may be used in the invention.

Note that to accommodate differing gerths and size, in order to enter patterns on the front and rear of the wearer, the mask is made up of two parts which interconnect on the sides of the wearer, with sufficient interlocking positions to accommodate a wide range of sizes with a single mask.

Figure 2A:
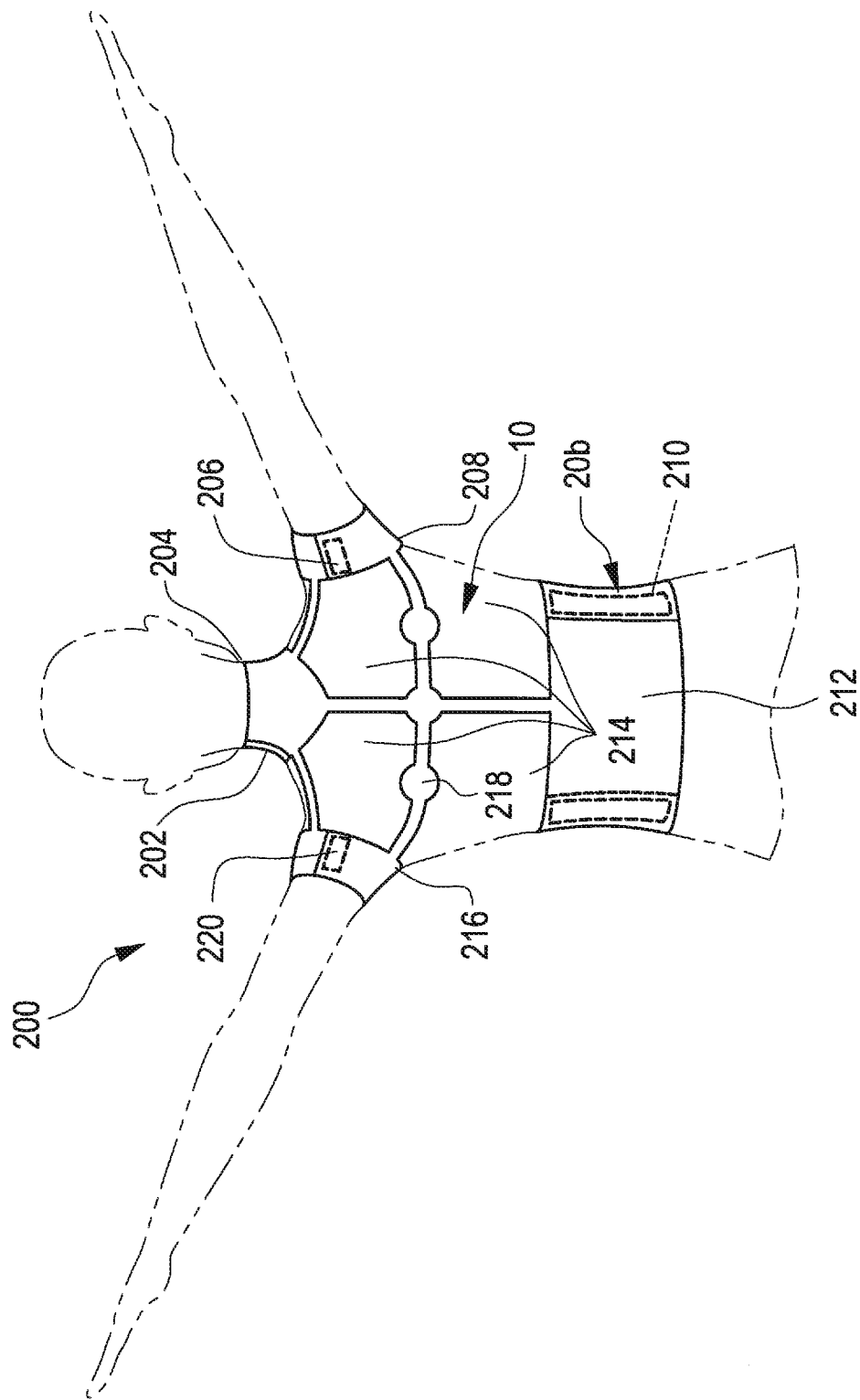
FIGS. 2A and 2B are three dimensional, perspective views of two mask variants of the invention, which if both used on a subject individual, create an interesting alternating pattern on the individual when two different color or applications, such as color and glitter are used.
Figure 2B:
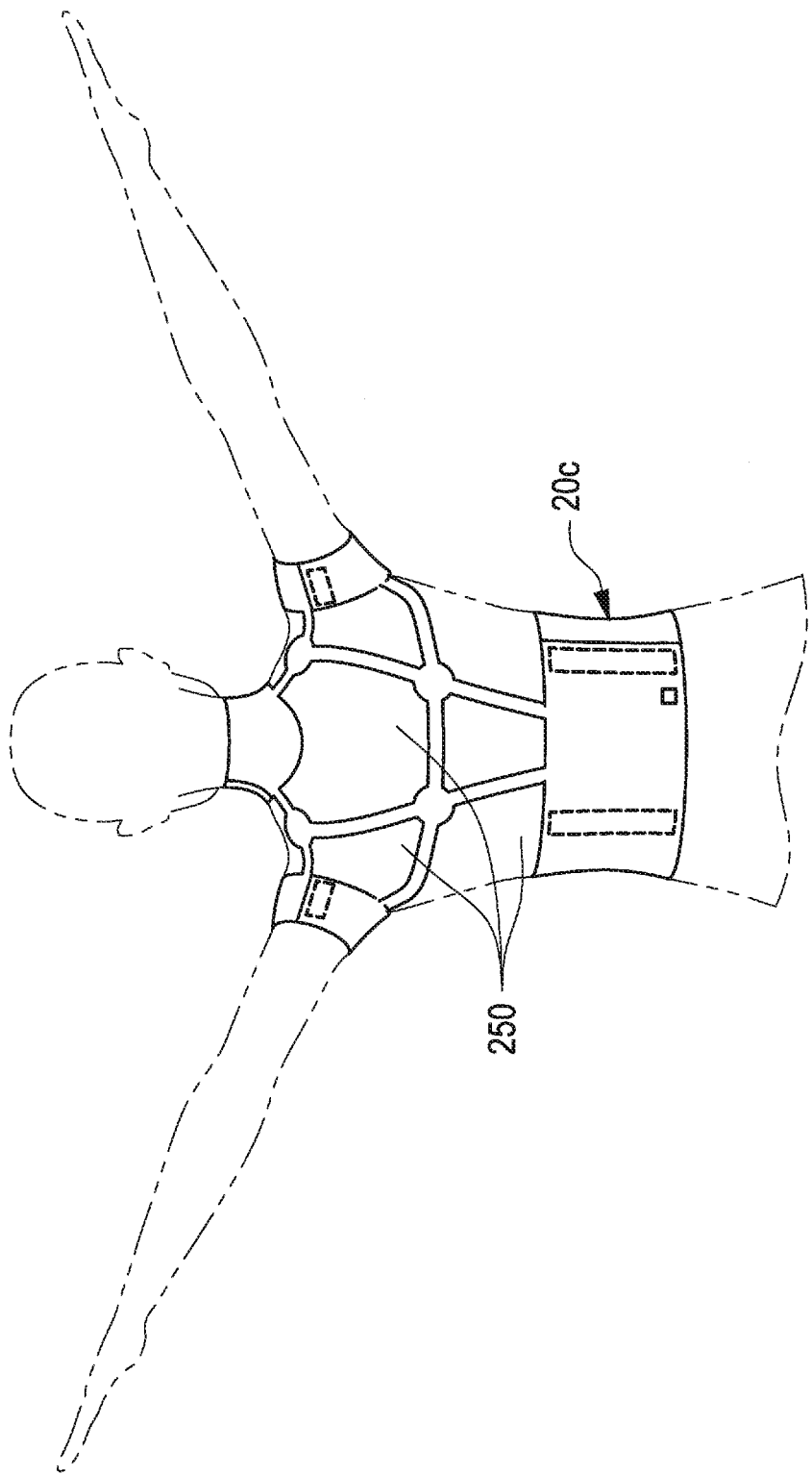

Referring now to FIGS. 2A and 2B, a three dimensional body painting system 200 is shown including a perspective view of two masks of the invention, which if both used on a subject individual, create an interesting alternating pattern on the individual when two different colors and/or applications, such as color and glitter (or other body adorning material) are used. The system 200 includes neck overspray panel 204 which, of course, includes an aperture for the placement of a human neck therein. The panel 204 is fastened around the neck with velcro element 202. Similarly, on the left sleeve overspray panel 208 is provided Velcro fastener 206. Chest overspray panel 212 is securely fastened into place around the chest of the user with velcrow fastener 210. Open spray areas 214 are provided as shown. It is appreciated that on system 200, the other stencil sub-systems as shown in FIGS. 1A and 1B are also provided. One or more pattern masks 218 are also provided on system 200. 216 right sleeve overspray panel is also joined by Velcro fastener 220. In the variant of system 200, in FIG. 2B, spray areas 250 are provided with various patterns being offset. This allows for an overlapping pattern effect and elements thereof to be provided. It is also possible to provide for an overlapping checkered pattern, by way of example.

Figure 3:
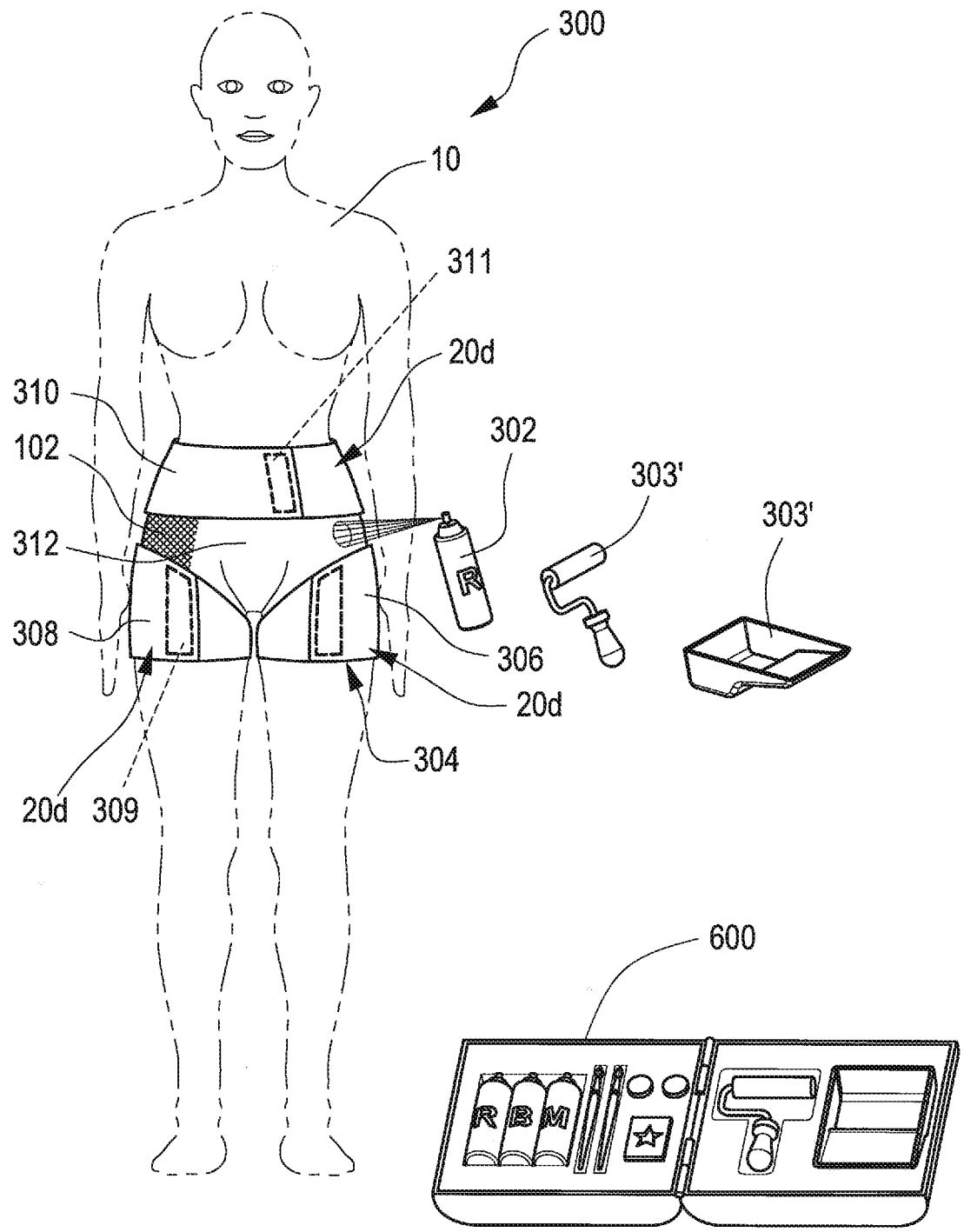
FIG. 3 is a front view of the system of the invention applied defining a bikini bottom area for painting, on a subject individual.

Referring now to FIG. 3, a front view of the system 300 of the invention is shown. Body spray paint is shown being applied so that it defines a bikini bottom area 312 for painting, on a subject individual. System 300 of the invention is sized, dimensioned and constructed with elements illustrated in the figures above, and body art spray can 302 is used in a method of the invention The system 300 indues a bottom portion 304, that includes a right thigh mask 308 and a left thigh mask 306. For example, right thigh mask 308 is provided with a Velcro fastener to join two ends of the mask. Left thigh mask 306 is provided with a Velcro fastener to join two ends of the mask. Waist mask 310 is provided with a Velcro fastener to join two ends of the mask. An exemplary method, as applied to the bikini area (but of course applies to any other area of the body also) is as follows: a method for applying a decorative paint to the epidermis of a human, the method comprising the steps of: applying a stencil having a decorative pattern formed therein around an appendage of a subject individual (in this figure the upper thighs and waiste), masking thereby a predetermined area of the epidermis, the stencil comprising an removable interlocking overlapping panel for enabling easy removal of the stencil, the stencil itself providing an opaque essentially non-absorbent layer which protects the underlying epidermal area from an applied body paint, defining further an epidermal painting area; covering the epidermal painting area and a portion of the non-absorbant layer of the stencil with a predetermined amount of an epidermal painting material to cause the epidermal painting material to contact the epidermis only via the decorative pattern masked by the stencil; allowing the epidermal painting material to dry, a portion of the epidermal painting material covering the portion of the epidermis that is coextensive with the decorative pattern masked by the stencil to form a decorative painting in the epidermis in the form of the decorative pattern; and removing the stencil from the subject individual, thereby leaving the painted decorative pattern.

Figure 4:
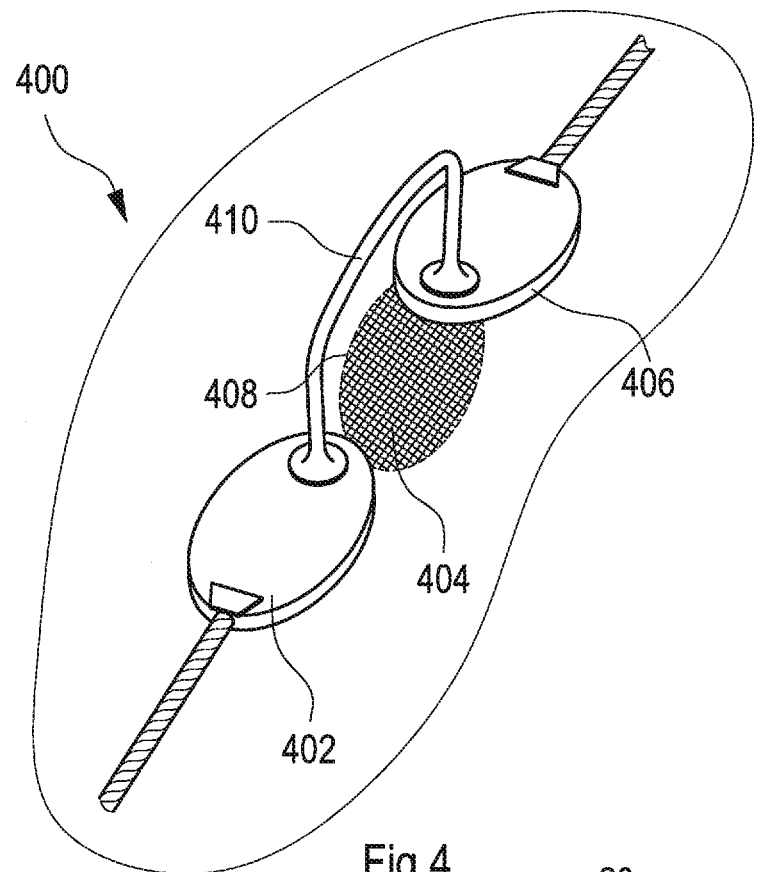
FIG. 4 is an example of a bridging element that supports two masks at defined locations with respect to one another while enabling color spraying thereunder.

Referring now to FIG. 4, an example of a sub-system 400 bridging element 410 that supports two masks 402, 406 is shown. The masks 402, 406 are disposed at defined locations with respect to one another while enabling color spraying thereunder. In this variant, pattern mask 402 is provided. A raised link 410 connects the patten mask 402 to pattern mask 406, and therebetween rests region of skin 408 which can be painted, e.g. otherwise it would be masked by the link that connects masks 402, 406. It is appreciated that one or more stencil designs herein utilize one or more or a network of raised (alone or in combination with non-raised bridging elements) bridging elements in a matrix to create very elaborate and detailed stencils on the human body in combinations heretofore unscene by the human eye. The height at which the raised link portion horizontal to the skin is placed varies upon the location at which the sub-system is used. It is appreciated that the height is variable, and can be from a millimetre upwards.

Figure 5:
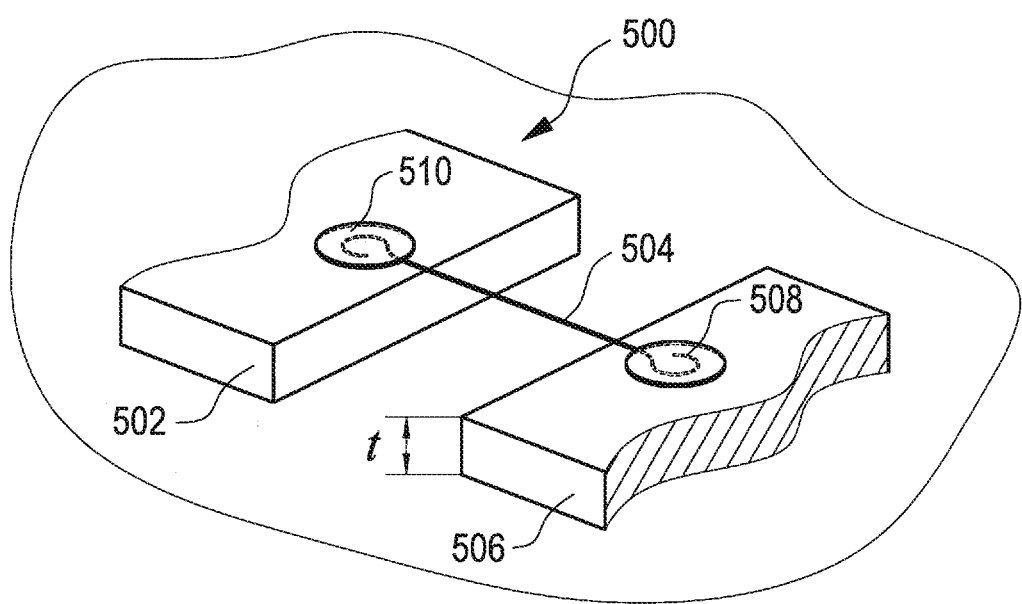
FIG. 5 is an example of another simple, nylon fishing line bridging element, which at least to a significant extent, allows for painting thereunder or which is sufficiently thin as not to mask any significant portion of the skin thereunder, allowing painting thereunder.

Referring now to FIG. 5, an example of sub-system 500 including another simple, nylon fishing line bridging element 504 is shown, which at least to a significant extent, allows for painting thereunder or which is sufficiently thin as not to effectively mask any significant portion of the skin thereunder, allowing painting thereunder. Sub-system 500 includes mask 502 which is connected to mask 506 by bridging element 504. Mask 502 (and other masks) are provided with a thickness of material "t" which raised bridging element 504 sufficiently above the skin so that aerosol spray particulates can be deposited on the skin under bridging element 504. Adhesive pads 508, 510 are used to fix bridging element 504 to the respective masks 502, 506. As with sub-system 400 it is appreciated that one or more syb-systems 500 are used to create one or more stencil designs herein, and utilize one or more or a network of raised (alone or in combination with non-raised bridging elements) bridging elements in a matrix to create very elaborate and detailed stencils on the human body in combinations heretofore unscene by the human eye in a manner that reduces the need for skilled artisanship and decreases time.

It is further appreciated that sub-systems 400, 500 (alone or in combination with other features of the invention) are used alone or in combination. In other variants of the invention, the sub-systems are used in a vertically stacked manner to provide for shading or areas of differing paint particulate deposits on the skin creating an even more detailed stencil design. In other variants, the sub-systems are used in prepositioned locations on the other systems of the invention, e.g. system 100, sysem 200, system 300, etc. One or more sub-systems are placed in series or parallel along systems 100, 200, 300, in yet further variants of the invention.

Figure 6:
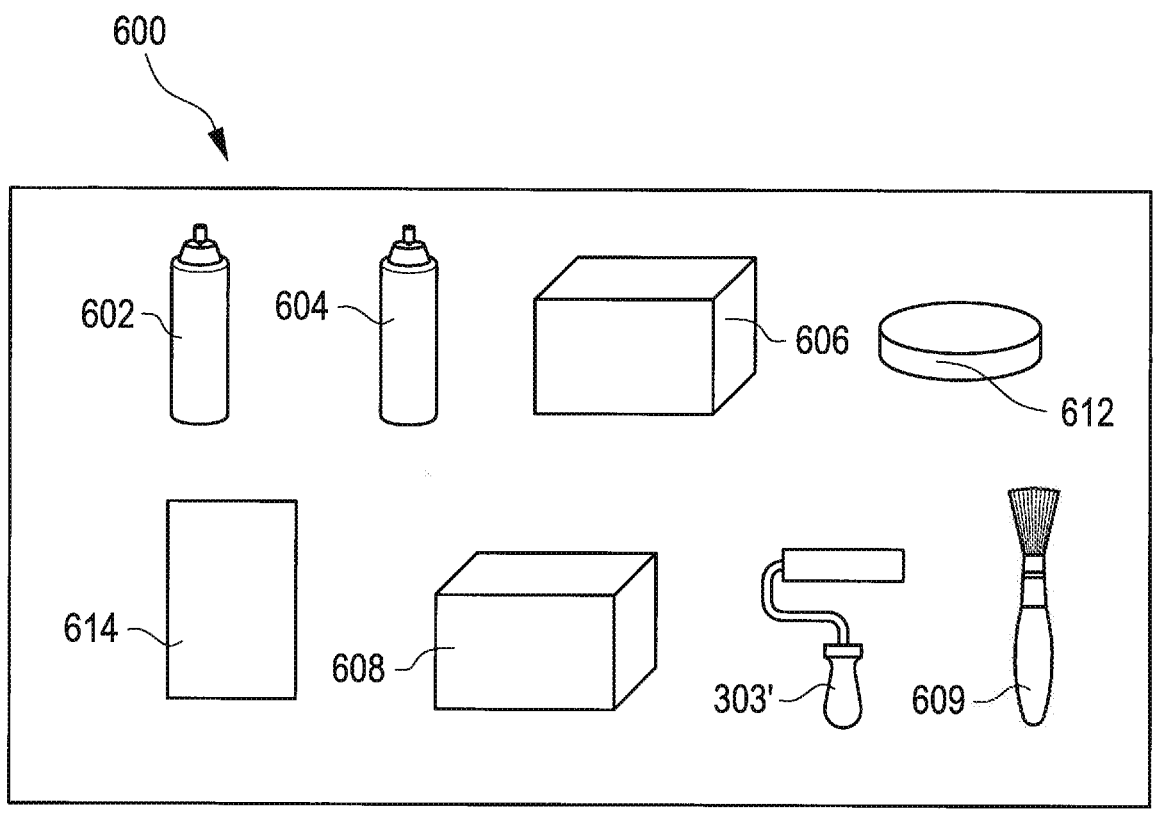
FIG. 6 is a scematic view of a kit of the invention.
Figure 7A:
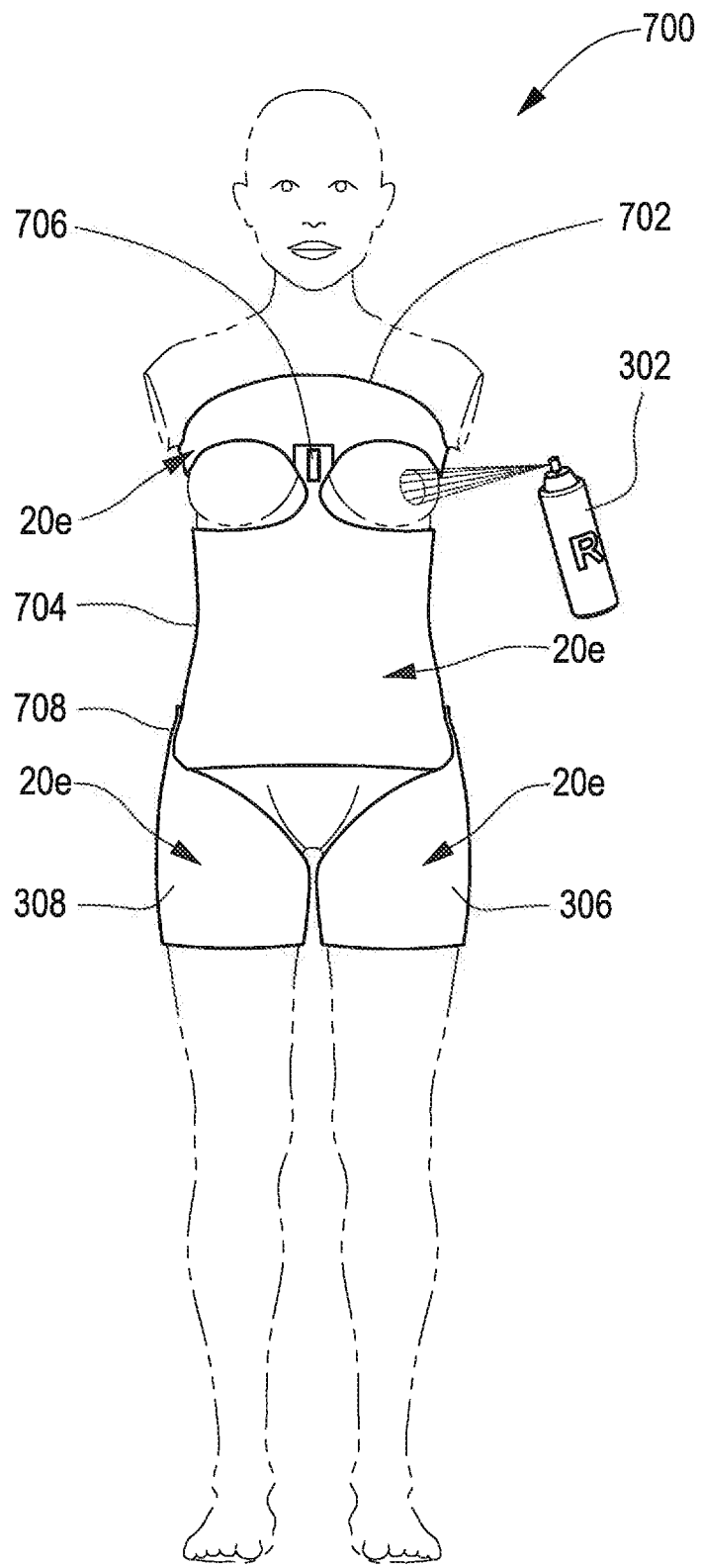
FIG. 7A is a front view of the mask in assembled form, mounted on a model or mannequin.
Figure 7B:
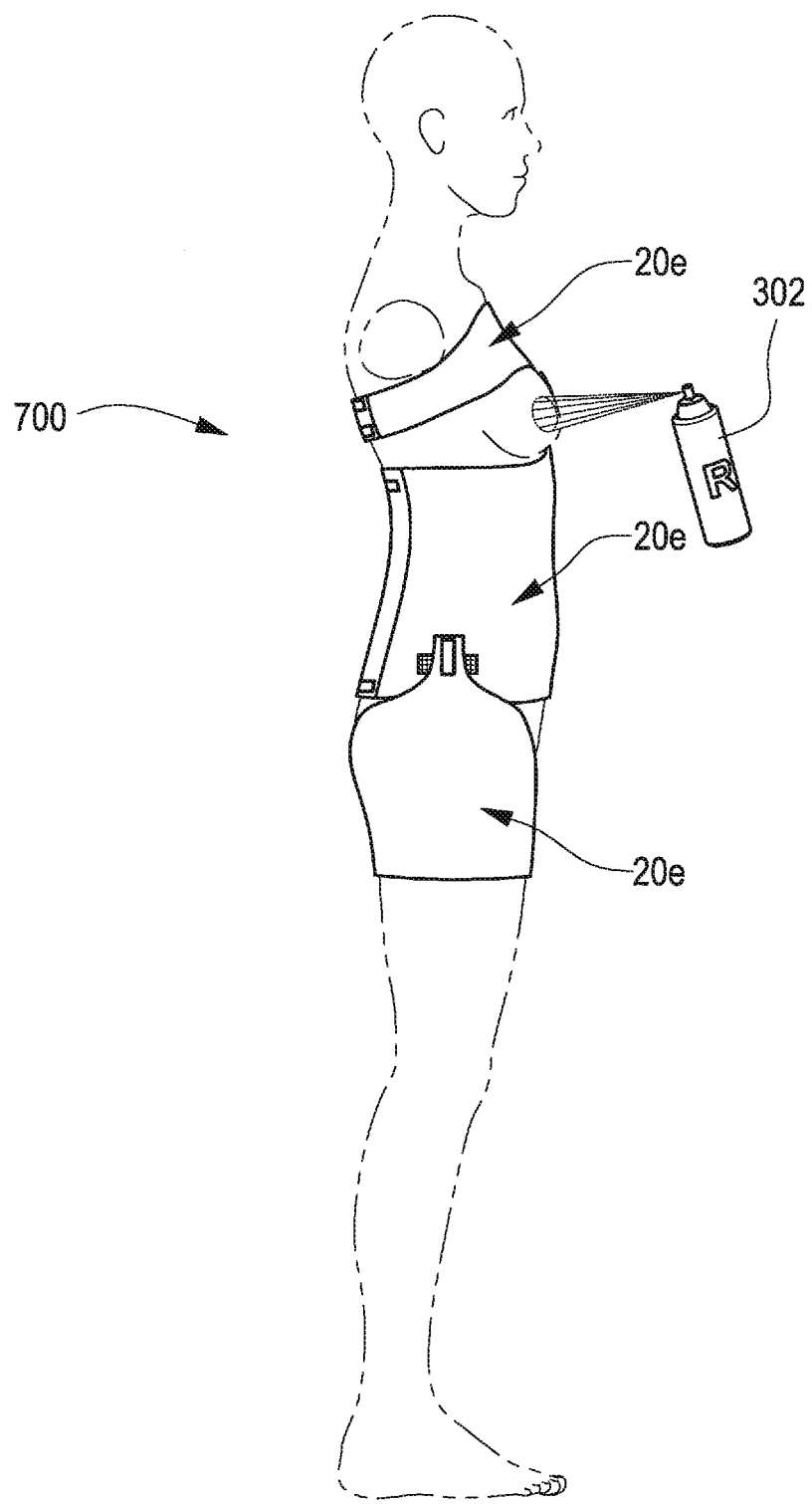
FIG. 7B is a right side view of the mask.
Figure 7C:
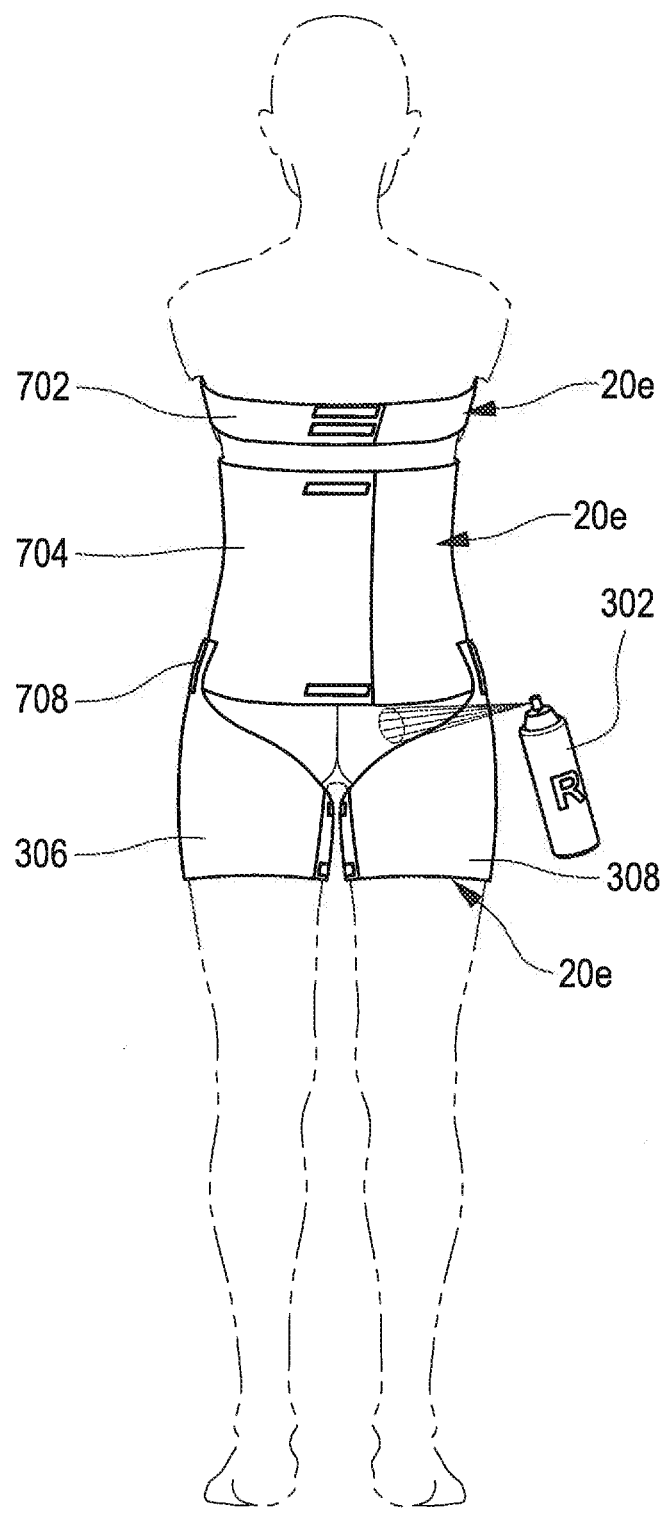
FIG. 7C is a rear view of the mask.
Figure 7D:
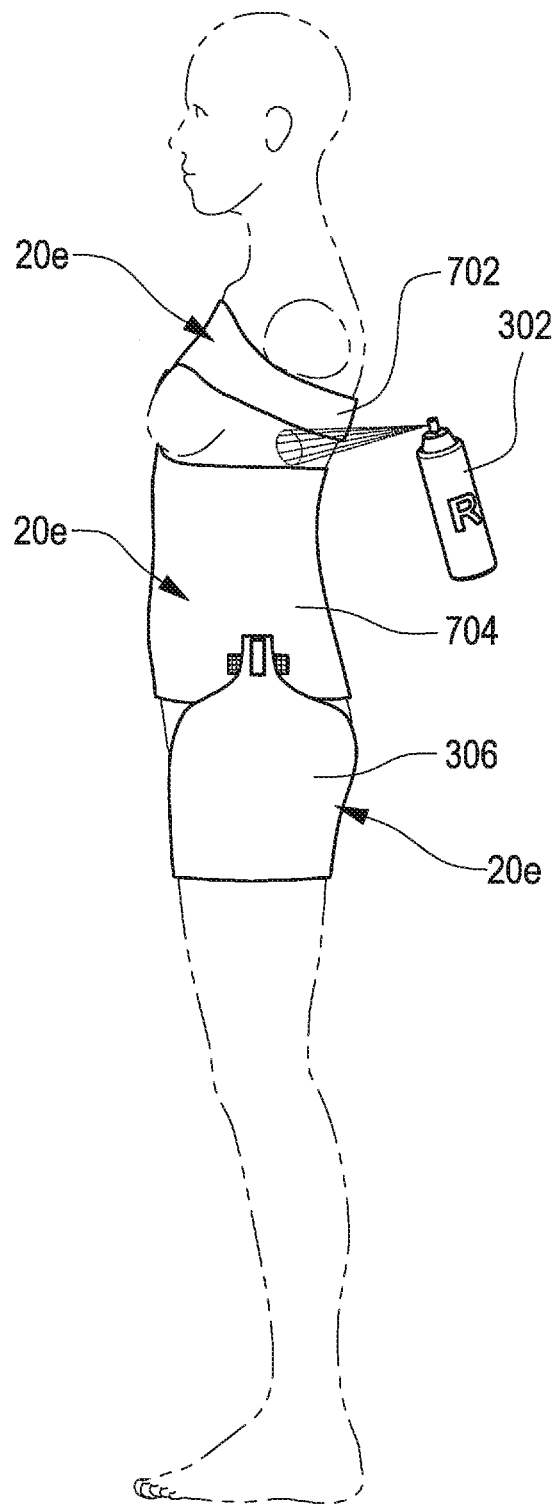
FIG. 7D is a left side view of the mask.
Figure 7E:
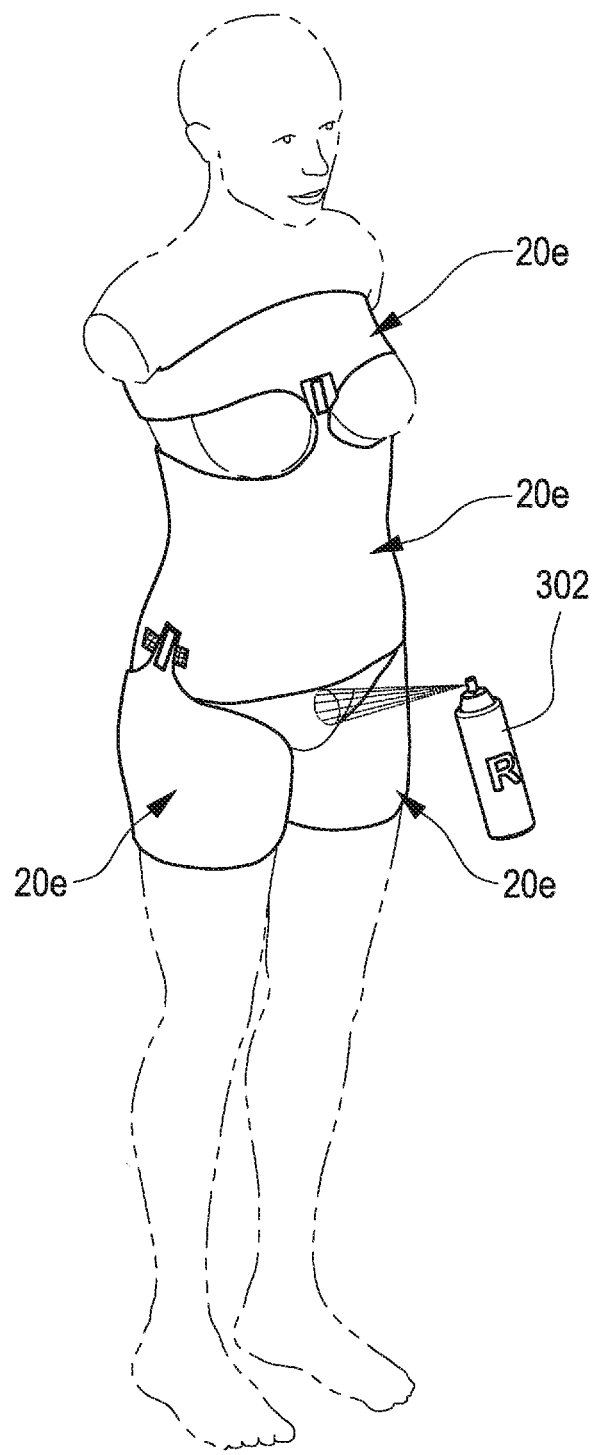
FIG. 7E is a top view of the mask.
Figure 7F:
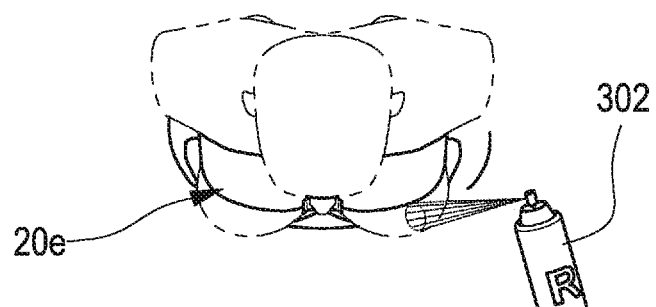
FIG. 7F is a rearward top view of the mask.
Figure 8A:
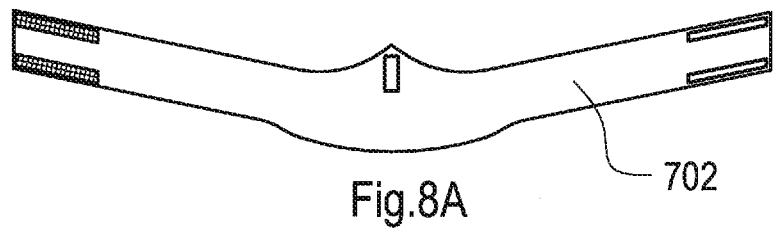
FIG. 8A is a top view of an upper component of the mask, laid flat.
Figure 8B:
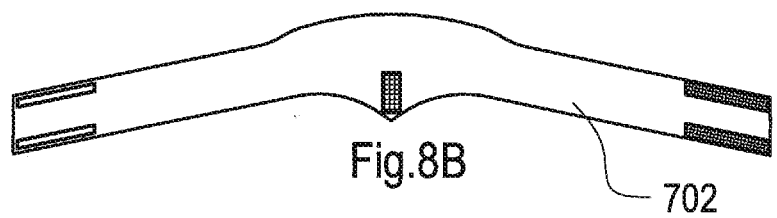
FIG. 8B is a bottom view of the upper component of the mask, laid flat.

Referring to FIG. 6, a kit 600 is shown, including body paint spray 602, fixing spray 604, one or more individual mask templates 606, 608 for application anywhere on the skin, the 3D masks 610 of the invention, and instructions for use including video demonstrations on DVD 612, for example. One or more elements of the kit 600 are used, alone or in combination with one or more other elements to form the kit depending on the specific body region that the particular kit is being used for, e.g. torso, waist, bikini area, legs, alone or in combination. In an embodiment, one or more masks of the invention are made of latex. In other embodiments, the mask is made of spandex or other stretchable, elastic material. In another embodiment, the mask is made of nylon stocking material. The interlocking is preferably made through a Velcro interlock, but other mechanical interlocking means, such as buttons, clasps, clips etc may be used. Further, adhesive and even magnetic means may be used to hold the mask in place against the skin.

It is further appreciated that kit 600 can include other elements to help round out the image or character created by the body art of the human. It is appreciated that this kit 600 is particularly useful during festivals, e.g. Carnavale in Brazil, and in other countries, as well as, a myriad of other events and festivals. With that in mind, the kit further optionally includes body painting colour material, and brushes; make up, and supporting application brushes, costume apparel, hair styling elements, in which the hair styling elements are selected from the group consisting of hair spray, hair colour spray, and a head dress, and footwear.

It should be also appreciated that the invention can be used in a process by which the stencil pattern is uploaded via the internet by the individual, and the system then manages the custom cutting (water or laser cutting for example) of the particular stencil pattern, along with other production, ancillary promotional, packaging, and mailing steps. The individual can also order any desired hair and body paint colors or glitter, to complete a desired order.

A further embodiment of the invention is shown in FIGS. 7A to 9B.

It should be appreciated that the particular implementations shown and herein described are representative of the invention and its best mode and are not intended to limit the scope of the present invention in any way.

Figure 10A:
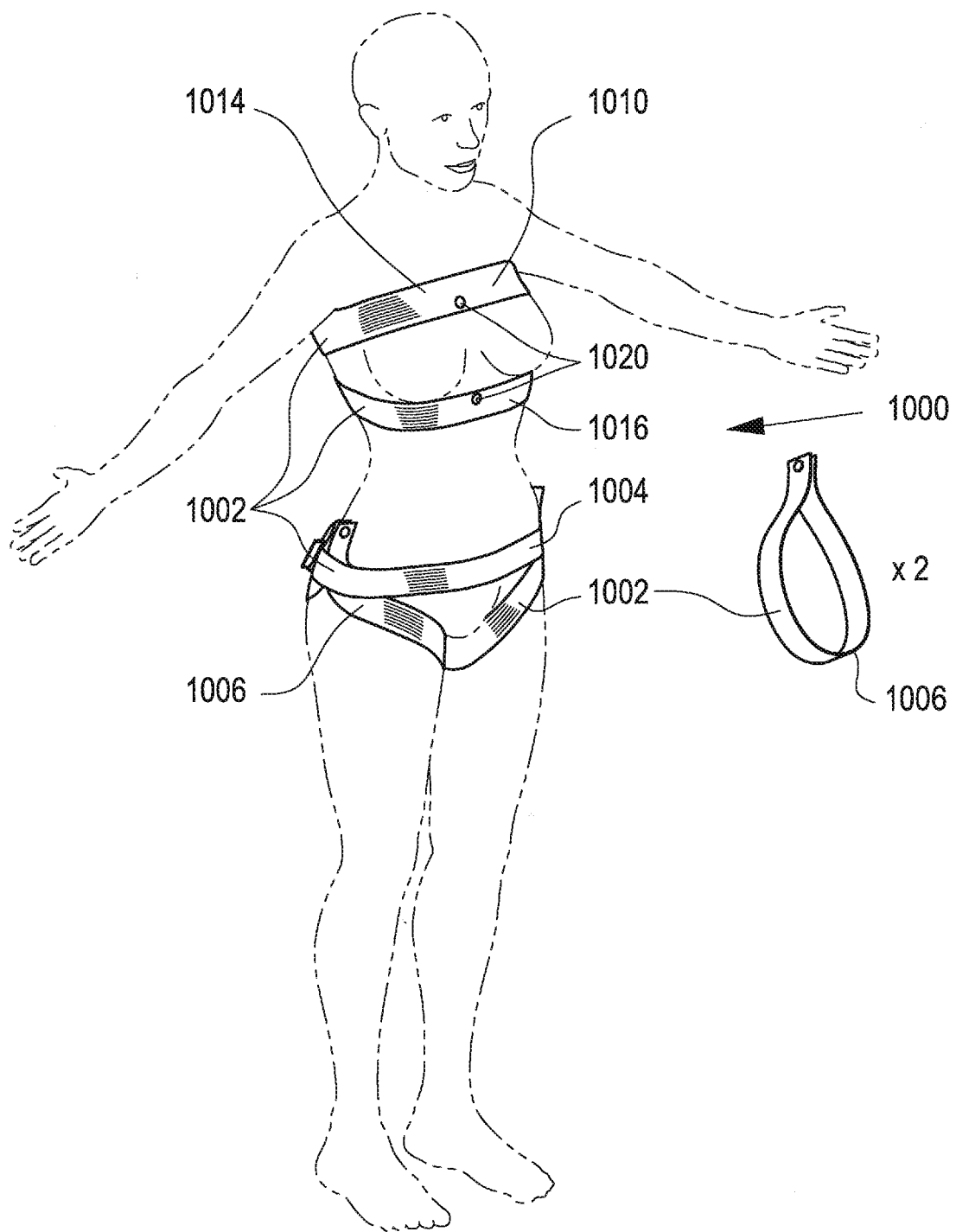
FIG. 10A is a perspective view of still another embodiment of the invention.
Figure 10B:
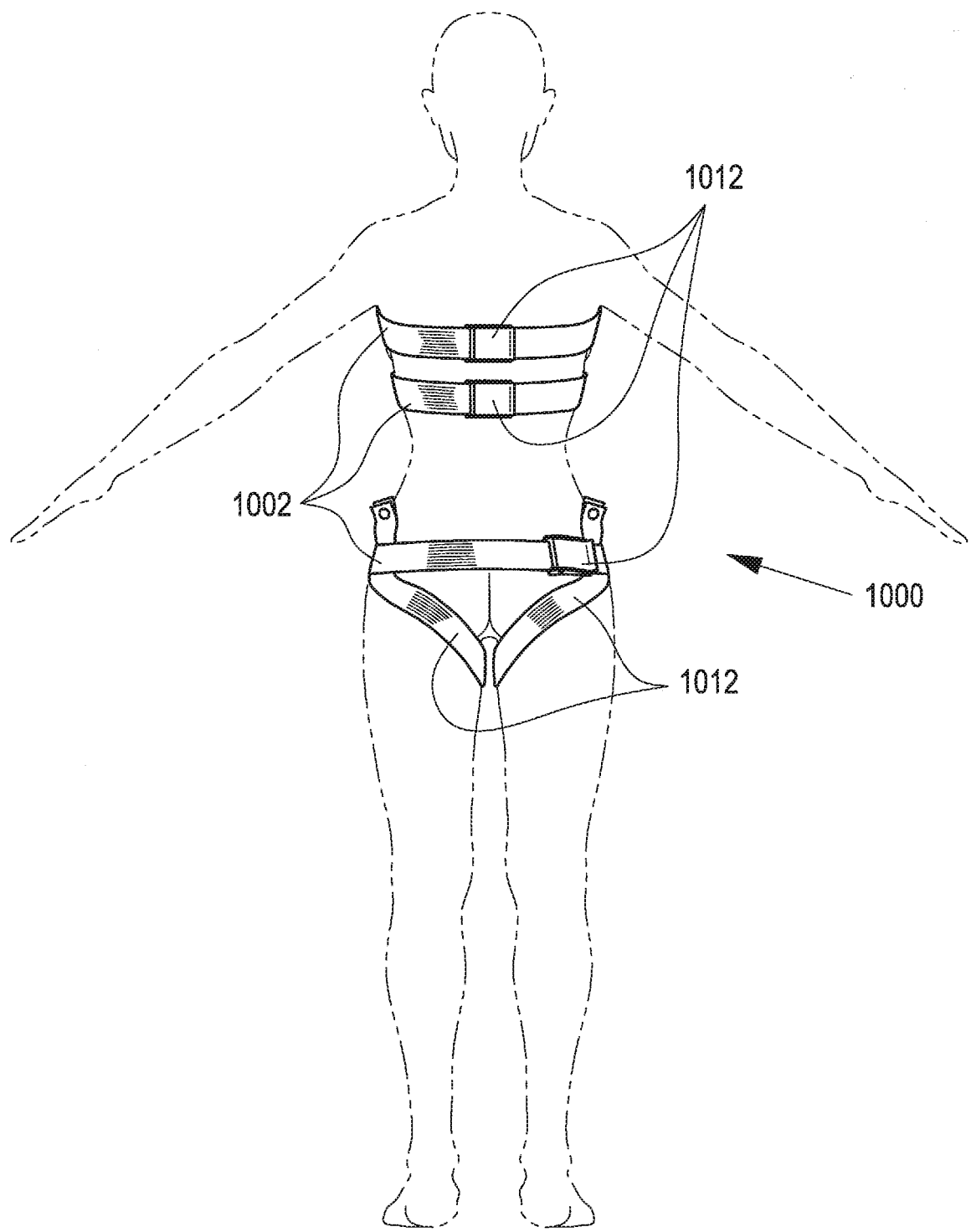
FIG. 10B is a rear view of the embodiment of FIG. 10A.
Figure 10C:
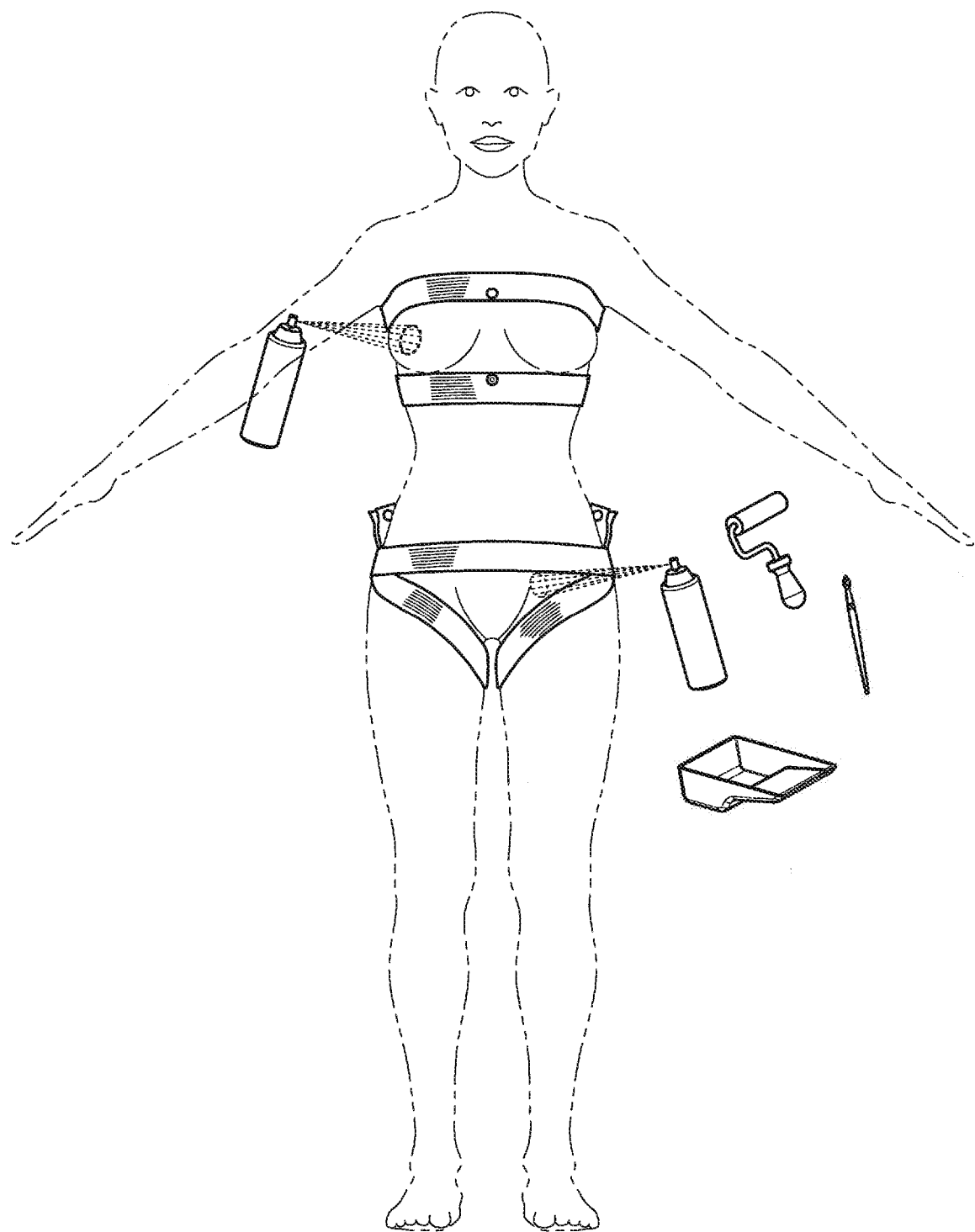
FIG. 10C is a front view of the embodiment of FIG. 10A.

Referring now to FIGS. 10A and 10B, in another embodiment 1000, wide elastic bands 1002, typically from 20 mm to 100 mm in width, preferably 50 mm in width, replace the more complicated forms of the proceeding embodiment. The elastic band material is preferably that used for underwear such as boxing shorts. The cut ends of the band material may be sewn, or a chrimpable trim component may be placed over and crimped on the end to give it a pleasing aesthetic appearance. At least one upper band 1004 and at least two thigh bands 1006 are required to mask a bathing suit form. In this embodiment, the upper band 1004, here disposed around the waist, includes a buckle 1012 (such as the one shown in FIG. 12E), allowing removal without disturbing freshly laid paint. The elasticity of the upper band 1004 allows the thigh bands 1006 to be tucked under the band 1004 and thereby held in place in an adjustable manner, where the portion of the thigh band 1006 which extends above the upper band 1004 may be pulled to draw up the band around the thighs, thereby creating a defined masked portion of a bikini bottom.

The thigh bands 1002 need not be bands but could be a truncated stocking portion where a tab on its side tucks under or otherwise attaches to the upper band 1004. This is possible because removal does not disturb the freshly painted area as the thigh portion is removed downwardly away from the painted area. In addition, the upper band 1004 may be easily removed by undoing the buckle 1012.

In order to mask a bikini form, two further elastic bands 1014, 1016 are required, which mask the bikini top area. These too are held around the body with a buckle 1012. An upper chest band 1014 is adapted to be positioned above the breast. A lower chest band 1016 is adapted to be positioned below the breast. The bands 1014, 1016 optionally have a fastening arrangement, in this case, two snaps or holes 1020 lined by eyelets through which a string 1102 (shown in FIG. 11) can pass to draw the two bands together in the area between the breasts.

Figure 10D:
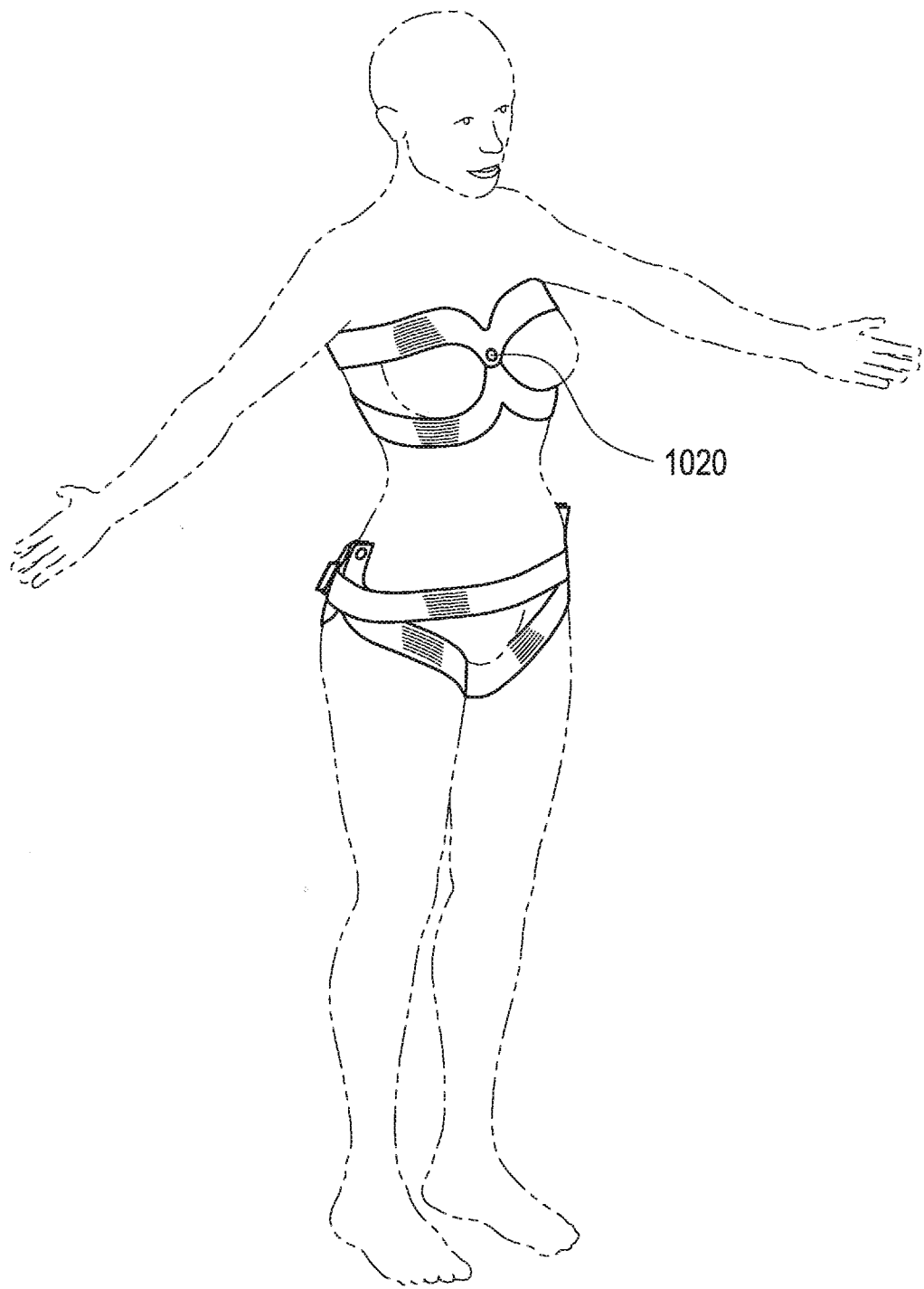
FIG. 10D is a front view of the embodiment of FIG. 10A with snaps closed.

Referring now to FIG. 10D, where snaps are used, the two bands may be snapped together in order to draw them together as shown.

Figure 11:
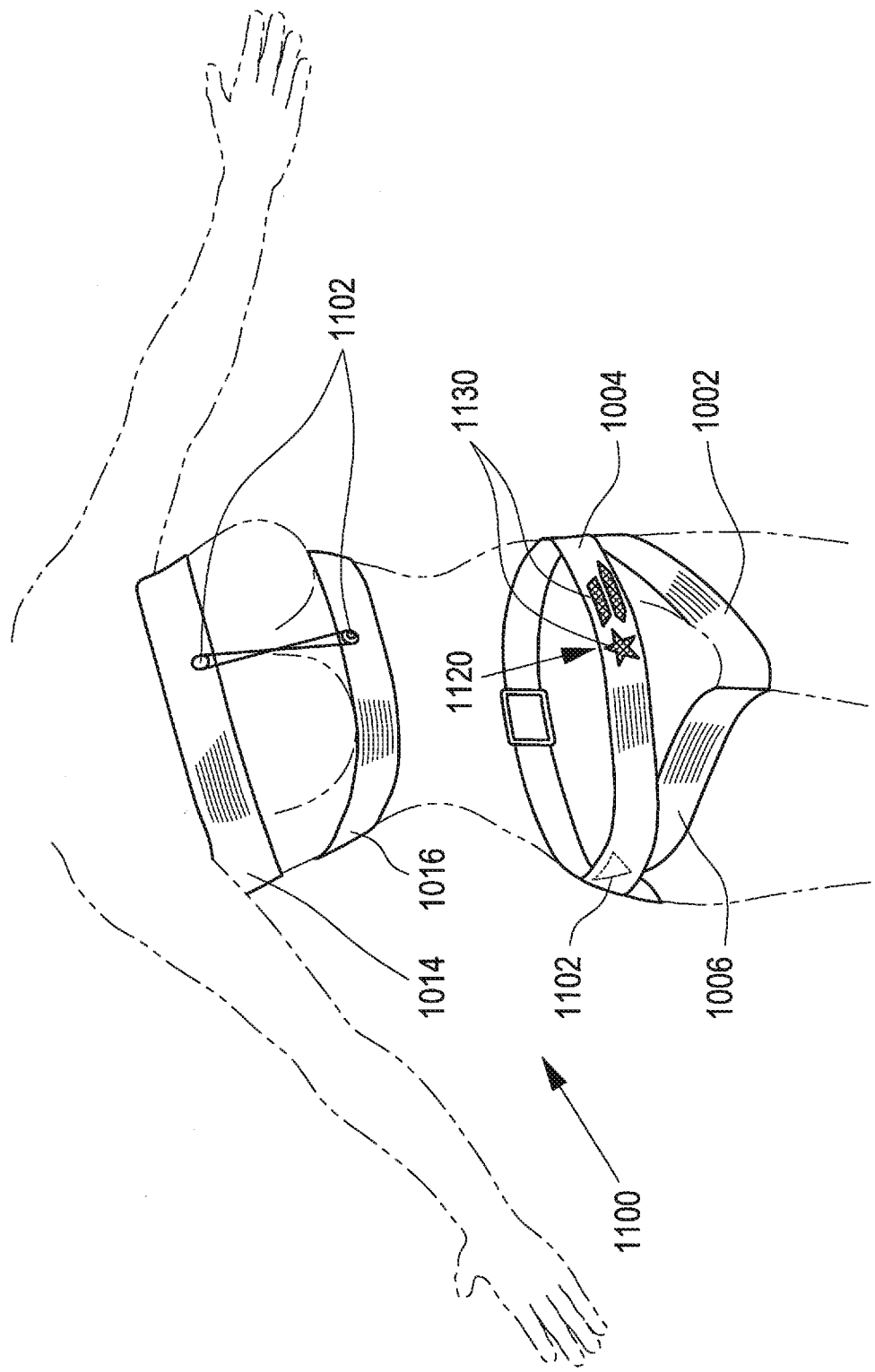
FIG. 11 is a perspective view of another embodiment of the invention.

Referring now to FIG. 11, in another variant 1100, the thigh bands 1002 are sewn, snapped, tided, stapled, interlocked, connected with hook and look connectors, glued, fused, or welded in place, such that other than the inherent flexibility of the bands 1002, the thigh bands 1002 are not adjustable. Some adjustability is obtained from the band 1004 as the buckle 1012 can be positioned on the band to be tighter or loser as the user prefers. Note that in this variant, a modified upper band 1004' is shown in which openings whose edges define a decorative pattern 1120 (in this case a star with two parallel lines) such as a logo or brand such as a sports team name, and which is held flat by a netting 1130. The wider the band 1004' is, the larger the decorative pattern can be.

Figure 12A:
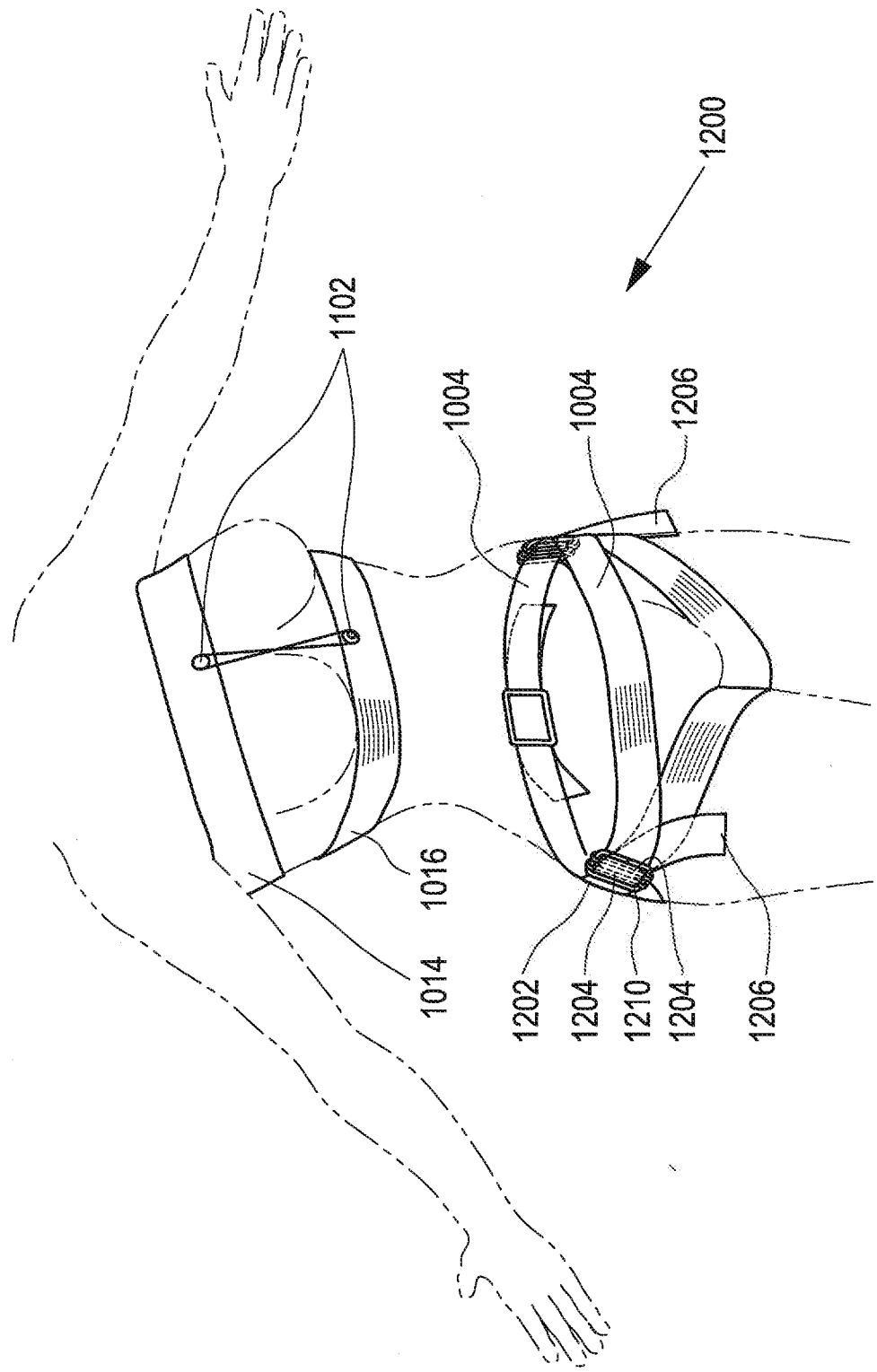
FIG. 12A is a perspective view of still another embodiment of the invention.
Figure 12B:
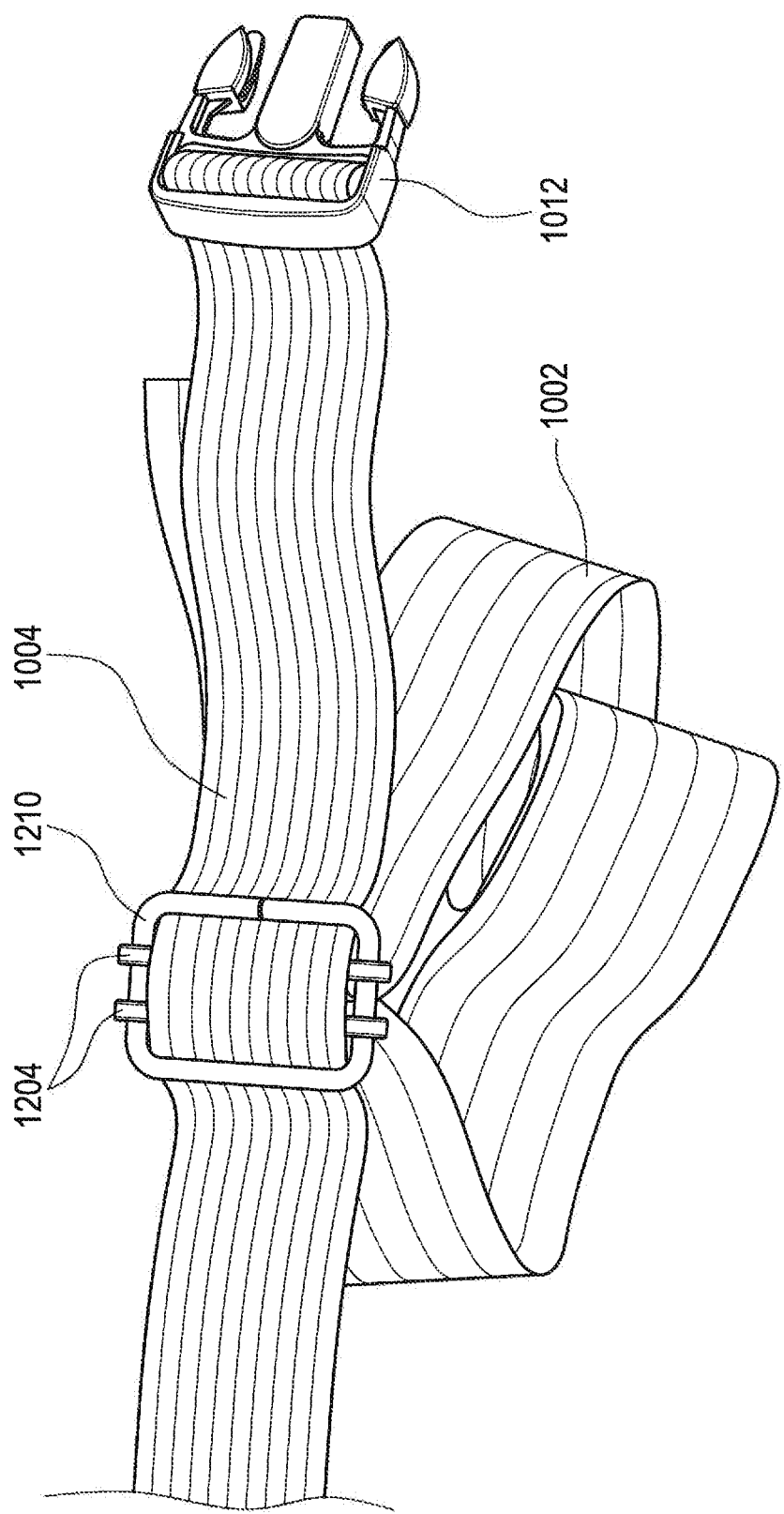
FIG. 12B is a side view of the hip area of the embodiment of FIG. 12A.
Figure 12D:
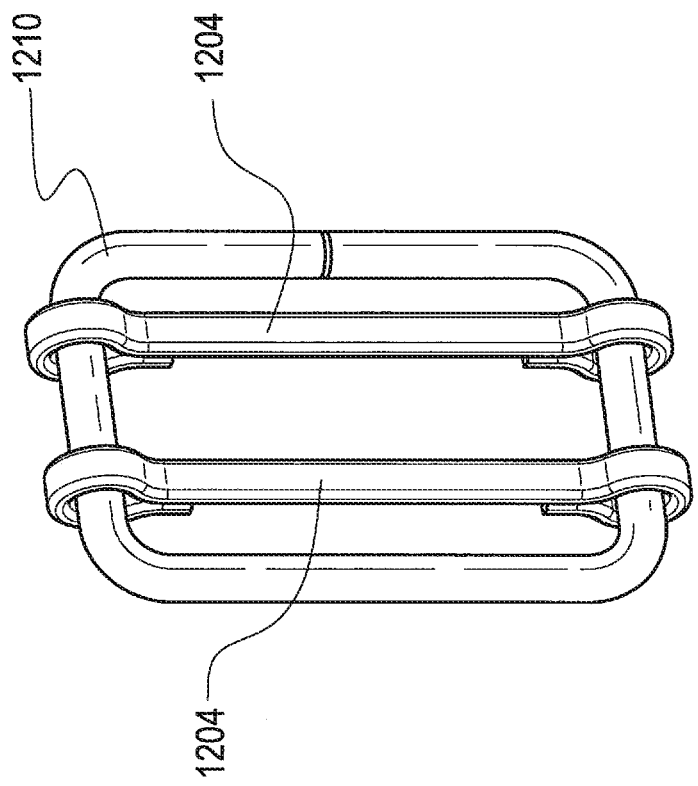
FIG. 12D is a close up view of the hip buckle used in the embodiment of FIG. 12A.
Figure 12E:
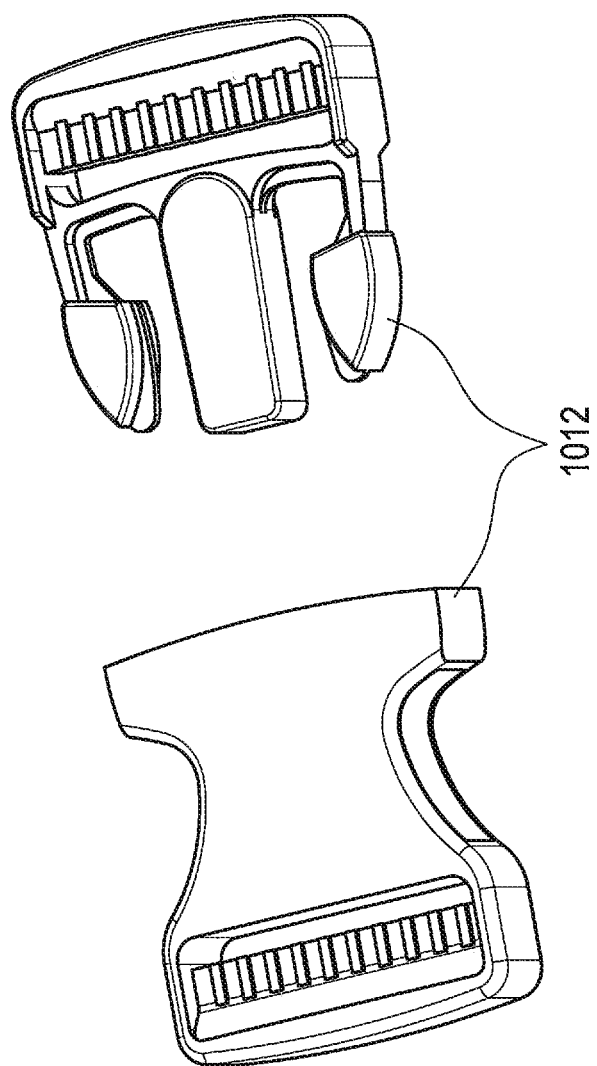
FIG. 12E is a close up view of the main waist buckle used in the embodiments of FIG. 12A.

Referring now to FIGS. 12A, 12B and 12C, in another variant 1200, the connection between the upper band 1004 and the thigh bands 1002 is effected with a double buckle 1202 (shown in more detail in FIG. 12D) which allows the upper band 1004 to pass through, will providing cross bars 1204 around which ends 1206 of the thigh bands 1002 pass and then under the upper band 1004 and the double buckle loop 1210. This allows a user to slide the double buckle 1202 along the upper band 1004 to a desired position, and to pull or release the ends 1206 of the thigh bands 1002 to adjust the fit of the thigh bands in order to obtain an more optimal and adjustable fitting of the stencil system of the invention.

Figure 13:
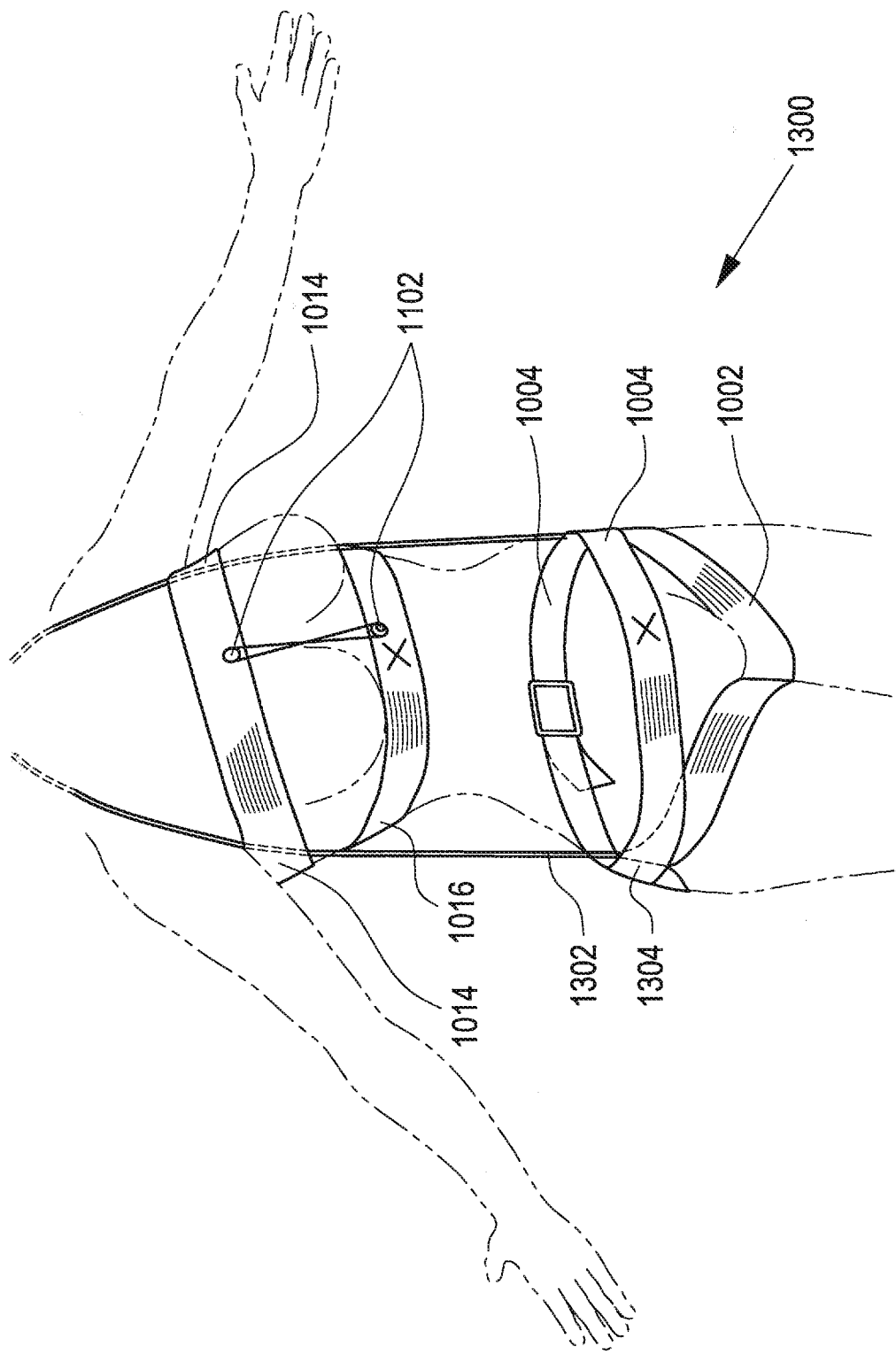
FIG. 13 is a perspective view of yet another embodiment of the invention using straps.

Referring now to FIG. 13, in another variant 1300, bands 1004 or 1016 are not required should a one piece swim suit form be masked. Instead, the thigh bands 1002 are held up with a strap 1302, preferably attached to a junction point 1304 of the thigh bands 1002, or straps (not shown) which go over the shoulders and reattach to the junction point 1304.

Moreover, the system contemplates the use, sale and/or distribution of any goods, services or information having similar functionality described herein.

As will be appreciated by skilled artisans, the present invention may be embodied as a system, a device, or a method.

Moreover, the system contemplates the use, sale and/or distribution of any goods, services or information having similar functionality described herein.

The specification and figures should be considered in an illustrative manner, rather than a restrictive one and all modifications described herein are intended to be included within the scope of the invention claimed. Accordingly, the scope of the invention should be determined by the appended claims (as they currently exist or as later amended or added, and their legal equivalents) rather than by merely the examples described above. Steps recited in any method or process claims, unless otherwise expressly stated, may be executed in any order and are not limited to the specific order presented in any claim. Further, the elements and/or components recited in apparatus claims may be assembled or otherwise functionally configured in a variety of permutations to produce substantially the same result as the present invention. Consequently, the invention should not be interpreted as being limited to the specific configuration recited in the claims.

Benefits, other advantages and solutions mentioned herein are not to be construed as critical, required or essential features or components of any or all the claims.

As used herein, the terms "comprises", "comprising", or variations thereof, are intended to refer to a non-exclusive listing of elements, such that any apparatus, process, method, article, or composition of the invention that comprises a list of elements, that does not include only those elements recited, but may also include other elements described in the instant specification. Unless otherwise explicitly stated, the use of the term "consisting" or "consisting of" or "consisting essentially of" is not intended to limit the scope of the invention to the enumerated elements named thereafter, unless otherwise indicated. Other combinations and/or modifications of the above-described elements, materials or structures used in the practice of the present invention may be varied or adapted by the skilled artisan to other designs without departing from the general principles of the invention.

The patents and articles mentioned above are hereby incorporated by reference herein, unless otherwise noted, to the extent that the same are not inconsistent with this disclosure.

Other characteristics and modes of execution of the invention are described in the appended claims.

Further, the invention should be considered as comprising all possible combinations of every feature described in the instant specification, appended claims, and/or drawing figures which may be considered new, inventive and industrially applicable.

Copyright may be owned by the Applicant(s) or their assignee and, with respect to express Licensees to third parties of the rights defined in one or more claims herein, no implied license is granted herein to use the invention as defined in the remaining claims. Further, vis-à-vis the public or third parties, no express or implied license is granted to prepare derivative works based on this patent specification, inclusive of the appendix hereto and any computer program comprised therein.

Additional features and functionality of the invention are described in the claims appended hereto. Such claims are hereby incorporated in their entirety by reference thereto in this specification and should be considered as part of the application as filed.

Multiple variations and modifications are possible in the embodiments of the invention described here. Although certain illustrative embodiments of the invention have been shown and described here, a wide range of changes, modifications, and substitutions is contemplated in the foregoing disclosure. While the above description contains many specific details, these should not be construed as limitations on the scope of the invention, but rather exemplify one or another preferred embodiment thereof. In some instances, some features of the present invention may be employed without a corresponding use of the other features. Accordingly, it is appropriate that the foregoing description be construed broadly and understood as being illustrative only, the spirit and scope of the invention being limited only by the claims which ultimately issue in this application.

What is claimed is:

1. A body stencil system having a body tight mask arrangement having at least four mask components for masking an area of a body for body painting, the mask components including an upper chest mask component adapted to extend around the upper chest under the armpits and above the breasts thereby masking an upper delimitation of a bathing suit form, at least one waist mask component extending around the waist to mask at least a lower delimitation of a bikini top form or an upper delimitation of a bikini bottom form and two thigh mask components each adapted to extend around a thigh to delimit a lower bathing suit form, wherein at least one of the mask components is an elastic band of a width in the range of between 20 mm and 100 mm.

2. The body stencil system of claim 1, wherein at least one of the mask components masks a decorative pattern defined by interior openings therein.

3. The stencil system of claim 2, wherein the interior openings are covered by a netting.

4. The body stencil system of claim 1, wherein the system includes at least one interlock selected from one of the group of interlocks consisting of adhesive, hook and loop fasteners, buttons, clasps, clips, magnets and other interlocking overlapping portions thereby enabling easy removal of the stencil without disturbing the freshly painted area.

5. A body stencil kit including the body stencil system of claim 1, further including at least one body paint and instructions for use.

6. The body stencil kit of claim 1, wherein the kit further includes detail stencils for applying further detailing over the basic painting or over otherwise unpainted areas.

7. A method for applying a decorative paint to the epidermis of a human, the method comprising the steps of:
    (a) applying the stencil system of claim 1 around a body of a subject individual, masking thereby a bathing suit pattern on the epidermis, the stencil system comprising the mask components which each mask a portion of the bathing suit pattern including at least the upper chest mask component adapted to extend around the upper chest under the armpits and above the breasts thereby masking the upper delimitation of the bathing suit form and the two thigh mask components each adapted to extend around a thigh to delimit the lower delimitation of the bathing suit form, the stencil system comprising removable interlocks for enabling easy removal of the mask components, the stencil system itself providing a layer which protects the underlying epidermal area from an applied body paint, defining further an epidermal painting area corresponding to the bathing suit pattern;

(b) covering the epidermal painting area with an epidermal painting material to cause the epidermal painting material to contact the epidermis only on the bathing suit pattern masked by the stencil system;

(c) allowing the epidermal painting material to dry; and (d) removing the stencil system from the subject individual, thereby leaving the painted bathing suit pattern.

8. The method of claim 7, wherein the epidermal painting material comprises a henna-based dye.

9. The body stencil system of claim 1, wherein the mask components are made of a material selected from one of the group of materials consisting of latex, neoprene, spandex, rubber or rubberized material, and nylon stocking material.

10. The stencil system of claim 1, wherein the mask components are connected together at least in part by a buckle which allows ready removal from a body of a wearer without disturbing an adjacent freshly painted area.

11. The body stencil system of claim 1, wherein the elastic band is of a width of 50 mm.

12. A body stencil system having a body tight mask arrangement having at least three mask components for masking against overspray an area of a body for body painting, the mask components including at least one upper mask component extending around an upper portion of the body to mask a portion of a bathing suit form and two thigh mask components each adapted to extend around a thigh to delimit a lower bathing suit form, wherein at least one of the mask components is an elastic band of a width in the range of between 20 mm and 100 mm.

13. The body stencil system of claim 12 wherein the mask components are made of a material selected from one of the group of materials consisting of latex, neoprene, spandex, rubber or rubberized material, and nylon stocking material.

14. The stencil system of claim 12, wherein the mask components are readily removable from a body of a wearer without disturbing an adjacent freshly painted area.

15. The body stencil system of claim 12, wherein the system includes at least one interlock selected from one of the group of interlocks consisting of adhesive, hook and loop fasteners, buttons, clasps, clips, magnets and other interlocking overlapping portions thereby enabling easy removal of the stencil without disturbing the freshly painted area.

16. The body stencil system of claim 12, wherein at least one of the mask components masks a decorative pattern defined by interior openings therein.

17. The stencil system of claim 16, wherein the interior openings are covered by a netting.

18. The body stencil system of claim 12, wherein a buckle attaches the thigh masks to the upper mask component in a slidable manner.

19. The body stencil system of claim 18, wherein the buckle includes attachment bars to which the thigh mask components attach.

20. The body stencil system of claim 19, wherein the thigh mask components attach to the attachment bars in an adjustable manner.

21. The body stencil system of claim 12, wherein the upper mask component is located above the chest and the thigh mask components include suspenders which hold the thigh mask components in place.

22. A body stencil kit including the body stencil system of claim 12, further including at least one body paint and instructions for use.

23. The body stencil kit of claim 22, wherein the kit further includes detail stencils for applying further detailing over the basic painting or over otherwise unpainted areas.

24. A method for applying a decorative paint to the epidermis of a human, the method comprising the steps of:

(a) applying the stencil system of claim 12 around a body of a subject individual, masking thereby a bathing suit pattern on the epidermis, the stencil system comprising the mask components which each mask a portion of the bathing suit pattern including at least the two thigh mask components each adapted to extend around a thigh to delimit the lower delimitation of the bathing suit form and at least an upper portion adapted to extend around the body to delimit the upper delimitation of the bathing suit form, the stencil system comprising removable interlocks for enabling easy removal of the mask components, the stencil system itself providing a layer which protects the underlying epidermal area from an applied body paint, defining further an epidermal painting area corresponding to the bathing suit pattern;

(b) covering the epidermal painting area with an epidermal painting material to cause the epidermal painting material to contact the epidermis only on the bathing suit pattern masked by the stencil system;

(c) allowing the epidermal painting material to dry; and (d) removing the stencil system from the subject individual, thereby leaving the painted bathing suit pattern.

25. The body stencil system of claim 12, wherein the elastic band is of a width of 50 mm.

* * * * *